US008815501B2

(12) United States Patent
Howley et al.

(10) Patent No.: US 8,815,501 B2
(45) Date of Patent: Aug. 26, 2014

(54) FLAVIVIRUS NS1 SUBUNIT VACCINE

(75) Inventors: Paul Howley, Glen Waverly (AU); Sonja Leyrer, München (DE); Mary Jane Cardosa, Kuching Sarawak (MY); Magdeline Sia Henry Sum, Kuching Sarawak (MY)

(73) Assignees: Bavarian Nordic A/S, Kvistgaard (DK); Venture Technologies SDN BHD, Sarawak (MY)

( * ) Notice: Subject to any disclaimer, the term of this patent is extended or adjusted under 35 U.S.C. 154(b) by 725 days.

(21) Appl. No.: 12/487,927

(22) Filed: Jun. 19, 2009

(65) Prior Publication Data

US 2010/0136054 A1 Jun. 3, 2010

Related U.S. Application Data

(60) Division of application No. 10/497,633, filed on Jun. 3, 2004, now Pat. No. 7,759,116, which is a continuation of application No. PCT/EP02/12991, filed on Nov. 20, 2002.

(30) Foreign Application Priority Data

Dec. 4, 2001 (DK) ................................ 2001 01804

(51) Int. Cl.
*C12Q 1/70* (2006.01)
*A61K 39/12* (2006.01)

(52) U.S. Cl.
USPC ....... 435/5; 424/199.1; 424/218.1; 435/320.1

(58) Field of Classification Search
CPC ................ A61K 39/12; A61K 39/295; A61K 2039/5256; A61K 2039/53; C12N 2770/24034; C12N 2770/24061; C12N 2770/24062; C12N 2770/24111; C12N 2770/24071; C12N 2770/24161; C12N 2770/24162; C12N 2770/24171
See application file for complete search history.

(56) References Cited

U.S. PATENT DOCUMENTS

| | | | |
|---|---|---|---|
| 5,494,671 | A | 2/1996 | Lai |
| 5,514,375 | A | 5/1996 | Paoletti |
| 5,744,140 | A | 4/1998 | Paoletti |
| 5,744,141 | A | 4/1998 | Paoletti |
| 5,824,506 | A | 10/1998 | Chan |
| 5,833,975 | A | 11/1998 | Pauoletti |
| 6,761,893 | B2 | 7/2004 | Chaplin |
| 6,869,793 | B2 | 3/2005 | Cardosa |
| 6,913,752 | B2 | 7/2005 | Chaplin |
| 7,097,842 | B2 | 8/2006 | Suter et al. |
| 7,759,116 | B2 | 7/2010 | Howley et al. |
| 2010/0047280 | A1 | 2/2010 | Howley et al. |

FOREIGN PATENT DOCUMENTS

| | | |
|---|---|---|
| GB | 2370573 | 7/2003 |
| WO | WO 9001946 | 3/1990 |
| WO | WO 9522978 | 8/1995 |
| WO | WO 97/02355 | 1/1997 |
| WO | WO 97/31119 | 8/1997 |
| WO | WO 9813500 | 4/1998 |
| WO | WO 99/07869 | 2/1999 |
| WO | WO 9915692 | 4/1999 |
| WO | WO 00/29428 | 5/2000 |
| WO | WO 0160847 | 8/2001 |
| WO | WO 0242480 | 5/2002 |

OTHER PUBLICATIONS

Bray et al., Mice Immunized with Recombinant Vaccinia Virus Expressing Dengue 4 Virus Structural Proteins with or without Nonstructural Protein NS1 Are Protected against Fatal Dengue Virus Encephalitis, Journal of Virology, Jun. 1989, p. 2853-2856.
Dmitriev et al., Immunization with recombinant vaccinia viruses expressing structural and part of the nonstructural region of tick-borne encephalitis virus cDNA protect mice against lethal encephalitis, Journal of Biotechnology 44 (1996) 97-103.
Zhao et al., Expression of Dengue Virus Structural Proteins and Nonstructural Protein NS1 by a Recombinant Vaccinia Virus, Journal of Virology, Dec. 1987, p. 4019-4022.
Antoine, et al. (1998) Virology 244:365-396.
Esposito, et al. (2004) Vaccinia virus strain Acambis 3000 Modified Virus Ankara (MVA), complete genome. GenBank Accession No. AY603355 (Header only).
Drexler, et al. (1999) Cancer Res. 59:4955-4963.
Sutter & Moss (1992) Proc Natl. Acad. Sci USA 89:10847-10851.
Carroll and Moss (1997) Virol. 238:198-211.-Abstract.
Mayr and Danner (1978) Deveolp. Biol. Standard 41:225-234.
Stittelaar, et al. (2001) Vaccine 19:3700-3709.
Staib & Sutter Live Viral Vectors:, in Methods in Molecular Medicine, vol. 87: Vaccine Protocols, 2nd Edn, Ed. A Robinson et al., Humana Press Inc, 2003.
Ramirez, et al. (2000) J. Virol. 74:7651-7655.
Men, et al. 2000, Vaccine 18:3113-3122.
Boukamp, et al. (1988) J. Cell Biol. 106:761-771.
VIVACS Project Report, Jun. 2005 (expert report, not prior art).
1999 Bavarian Nordic Annual Report (pp. 1-4), published Mar. 2000.
2000 Bavaian Nordic Annual Report (pp. 1-4), published Mar. 2001.
Article in Pharmaceutical Business Review Online Dec. 20, 2004.
Rosenwirth, et al. (1999) J. Med. Promatol. 28:195-205.
Hirsch, et al. (1996) J. Virol. 70:3741-3752.
Jackson, et al. (1995) J. Exp. Med. 182:751-758.

(Continued)

*Primary Examiner* — Stacy B. Chen
(74) *Attorney, Agent, or Firm* — Law Office of Salvatore Arrigo and Scott Lee, LLP

(57) ABSTRACT

The present invention relates to NS1 proteins or parts thereof of Flaviviruses, in particular of Dengue viruses useful for vaccination against said Flavivirus and against one or more other Flaviviruses. The invention further concerns the NS1 protein or parts thereof of one Dengue virus serotype, in particular serotype 2, useful for vaccination against Dengue viruses from all serotypes. The invention further concerns DNA comprising an expression cassette coding for a Flavivirus NS1 or parts thereof, vectors comprising said DNA and vaccines containing or expressing a Flavivirus NS1.

18 Claims, 9 Drawing Sheets

(56) References Cited

OTHER PUBLICATIONS

Figure 1B:
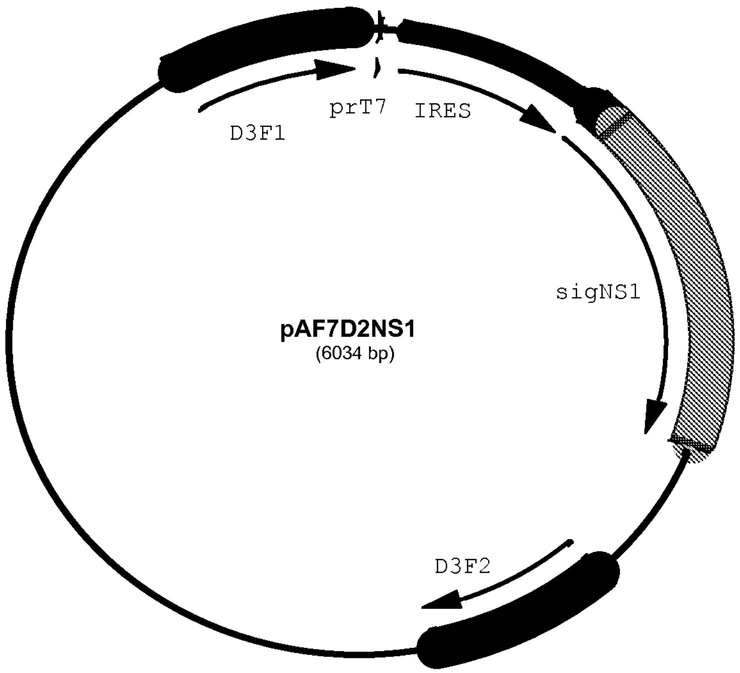

Schlesinger JJ, et al.: Journal of General Virology, vol. 68, No. 3, 1987, pp. 853-858.
Chambers JT, et al.: Vaccine, Butterworth Scientific. Guildford, GB, vol. 15, No. 14, Oct. 1, 1997, pp. 1494-1502.
Bray M. et al.: Journal of Virology, vol. 70, No. 6, 1996, pp. 4162-4166.
Falconar AK., et al.: Journal of General Virology, Reading, Berks, GB, vol. 72, No. 4, Apr. 1991, pp. 961-965.
NCBI Nucleotide Sequence, Accession No. AF204178 Dengue virus type 2 strain 43, complete genome. Hu, et al. (1999)-Header only.
Letter Jun. 28, 2005 from patentte to EPO on appin No. 97943887.6.
Kinney et al., Intervirology, 2001, 44(2/3):176-197.
Verma et al., Nature, 1997, vol. 389, pp. 239-242.
Orkin et al., report and Recommendation of the Panel to Assess the NIH Investment on Gene Therapy, NIH, 1995, 39 pages from the website printout: www.nih.gov/news/panlrep.html.
In the matter of: Certain Modified Vaccinia Ankara ("MVA"), Investigation No. 337-TA-550, Order No. 28, United States International Trade Commission, Apr. 18, 2006.
In the matter of: Certain Modified Vaccinia Ankara ("MVA"), Investigation No. 337-TA-550, Nucleotide alignment of MVA-Antione vs Acambis 3000 MVA vs MVA-BN, Aug. 31, 2005.
In the matter of: Certain Modified Vaccinia Ankara ("MVA"), Investigation No. 337-TA-550, Respondent's Amended Pre-Hearing Brief, May 8, 2006.
In the matter of: Certain Modified Vaccinia Ankara ("MVA"), Investigation No. 337-TA-550, Respondent's Opposition to Complainant's Motion for Sanctions, Jul. 7, 2006.
In the matter of: Certain Modified Vaccinia Ankara ("MVA"), Investigation No. 337-TA-550, Respondent's Rebuttal to Compainant's Proposed Conclusions of Law, Jun. 14, 2006.
In the matter of: Certain Modified Vaccinia Ankara ("MVA"), Investigation No. 337-TA-550, Complainant's Motion for Sanctions and Memorandum, Jun. 21, 2006 (Public Version).
In the matter of: Certain Modified Vaccinia Ankara ("MVA"), Investigation No. 337-TA-550, Memorandum in Opposition to Respondent's Motion, Mar. 30, 2006 (Public Version).
In the matter of: Certain Modified Vaccinia Ankara ("MVA"), Investigation No. 337-TA-550, Complainant's Memorandum in Support of Its Motion in Limine, May 1, 2006 (Pub. Ver.).
In the matter of: Certain Modified Vaccinia Ankara ("MVA"), Investigation No. 337-TA-550, Complainant's Post Hearing Brief, Apr. 28, 2006 (Public Version).
In the matter of: Certain Modified Vaccinia Ankara ("MVA"), Investigation No. 337-TA-550, Complainant's Motion for Summary Determination and Memo, Mar. 20, 2005 (Pub.Vers.).
In the matter of: Certain Modified Vaccinia Ankara ("MVA"), Investigation No. 337-TA-550, Complainant's Post Hearing Reply Brief, Jun. 14, 2006 (Public Version).
Bender, et al., Oral Immunization with a Replication-Deficient Recombinant Vaccinia Virus Protects Mice Against Influenza. (1996) J. Virology, vol. 70(9):6418-6424.
Drillien, et al, Attenuation Profile Comparison of Various MVA Strains. Study Report, Institut de Genetique et de Biologie Moleculaire et Cellulaire, France, Feb. 22, 2006.
Hulsemann, et al., Attenuation Profile Comparison of Various MVA Strains. Project #1050, Bavarian Nordic GmbH, Martinsried, Germany, Jan. 2006.
"Determination of various growth charact . . . " VIVACS Study Plan, Project #0100506 and VIVACS Study Report, SR-0100506-01,VIVACS GmbH, Martinsried, Germany, Feb. 2006.
VIVACS Studyplan, Project #1200405, VIVACS Study Report, SR-AM-1200405-00, Amendment to VIVACS Study Report SR-AM02-1200405-00VIVACS GmbH, Martinsried, Germany, Jan. 2006.
Zinkernagel. et al., "Attenuation Profile Comparison of Various MVA-strains." Study Report UA_02_06, University of Zurich, Zurich Switzerland, Mar. 2006.
Antione, G. "Differences in DNA sequence of MVA Acambis AY603355 relative to MVA Antione et al (U94848)." Baxter Report—Mar. 31, 2006.
Antione. et al. Corrigendum to "The complete genomic sequence of the Modified Vaccinia orthopoxviruses" Virology 244 (1998) 365-396. Baxter Bioscience, BO08572.
"PCR-Amplification and Double Strand Sequencing of Five Genomic Regions of M4-MVA U94848." Analytical Report, Project No. KN-639, GATC Biotech AG, Germany, May 9, 2006.
Sequence Report-MVA 572, Sequiserve, Vetterstetten, Germany, Jul. 6, 2006.
Sequence Report-MVA-1721, Sequiserve, Vetterstetten, Germany, Jul. 6, 2006.
Drexler, et al., J. Gen. Virol. (1998) 79:347-352.
International Preliminary Examination Report, dated Jan. 11, 2006, four (4) pages.
Tartaglia, et al. "NYVAC: a highly attenuated strain of vaccinia virus" Virology 1992, vol. 188, pp. 217-232.
Kovarik, et al. "Induction of adult-likeantibody, Th1, and CTL responses to measles hemaglutinin . . . " Virology Jun. 20, 2001, vol. 285, pp. 12-20.
Kazanji, et al. "Immunogenicity and protective efficacy of recombinant human . . . " Journal of Virology, Jul. 2001, vol. 75(13), pp. 5939-5948.
U.S. International Trade Commission, Inv. No. 337-TA-550, Order No. 10: Denying Respondent's Motion to Terminate and Entry of Consent Order, Nov. 30, 2005, pp. 1-8.
Inv. No. 337-TA-550, Complainant Bavarian Nordic's Motion for Summary Determination of Infringement of the '893 Patent, Mar. 20, 2005, pp. 1-15.
U.S. International Trade Commission, Inv. No. 337-TA-550, Complainant's Petition for Review of the Final Initial Determination, Sep. 18, 2006, pp. 1-52.
U.S. International Trade Commission, Inv. No. 337-TA-550, Order No. 16: Granting Complainant's Motion to Declassify Confidential Information, Feb. 15, 2006, pp. 1-8.
U.S. International Trade Commission, Inv. No. 337-TA-550, Bavarian Nordic's Complaint Under Section 337 of the Tariff Act of 1930, Aug. 19, 2005, pp. 1-30.
Federal Register, vol. 70, No. 184, Sep. 23, 2005, pp. 55918-55919.
U.S. International Trade Commission, Inv. No. 337-TA-550, Memorandum in Opposition to Respondent's Motion to Terminate, Nov. 28, 2005, pp. 1-17.
U.S. International Trade Commission, Inv. No. 337-TA-550, Memorandum in Support of Respondent's Motion for Summary Determination, Mar. 30, 2005, pp. 1-48.
U.S. ITC, Inv. No. 337-TA-550, Appendix to Memorandum in Support of Respondent's Motion for Summary Determination, vol. 1 of 3, Oct. 31, 2005, pp. 1-64.
U.S. ITC, Inv. No. 337-TA-550, Appendix to Memorandum in Support of Respondent's Motion for Summary Determination, vol. 2 of 3, Dec. 1, 2005, pp. 1-45.
U.S. International Trade Commission, Inv. No. 337-TA-550, Notice of Investigation, Sep. 19, 2005.
U.S. International Trade Commission, Inv. No. 337-TA-550, Respondent's Opposition to Complainant's Motion to Declassify Confidential Information, Feb. 13, 2006, pp. 1-9.
U.S. ITC, Inv. No. 337-TA-550, Motion for Leave to File Reply, Respondent's Certification, and Reply, Apr. 5, 2005 (pp. 1-3), Apr. 5, 2006.
U.S. International Trade Commission, Inv. No. 337-TA-550, Respondent's Notice of Prior Art, Feb. 3, 2006, pp. 1-8.
U.S. ITC, Inv. No. 337-TA-550, Response of Acambis plc Under Section 337 of the Tariff Act of 1930 and Notice of Investigation, Oct. 21, 2005, pp. 1-24.
U.S. International Trade Commission, Inv. No. 337-TA-550, Commission Investigative Staffs Response to the Private Parties' Motions in Limine, May 3, 2006, pp. 1-5.
U.S. International Trade Commission, Inv. No. 337-TA-550, Commission Investigative Staffs Notice of Prior Art, Feb. 3, 2006.
U.S. International Trade Commission, Inv. No. 337-TA-550, Consent Order Stipulation, Nov. 2, 2005, pp. 1-4.

(56) References Cited

OTHER PUBLICATIONS

U.S. International Trade Commission, Inv. No. 337-TA-550, Consent Order Stipulation (pp. 1-4) with Commission Opinion of Feb. 21, 2007, pp. 1-39.
U.S. International Trade Commission, Inv. No. 337-TA-550, Office of Unfair Import Investigation's Response to Commission Notice of Jan. 19, 2007, Jan. 26, 2007, pp. 1-8.
U.S. ITC, Inv. No. 337-TA-550, Office of Unfair Import Investigations' Combined Response to Responses to Questions Posed by the Commission, Dec. 22, 2006, pp. 1-23.
U.S. ITC, Inv. No. 337-TA-550, Office of Unfair Import Investigations' Response and Briefing on the Issues of Remedy, Public Interest, and Bonding, Dec. 12, 2006, pp. 1-30.
U.S. ITC, Inv. No. 337-TA-550, Initial Determination on Violation of Section 337 and Recommended Determination on Remedy and Bonding, Sep. 6, 2006.
U.S. International Trade Commission, Inv. No. 337-TA-550, Respondent's Post-Hearing Brief, Aug. 15, 2006, pp. 1-80.
U.S. ITC, Inv. No. 337-TA-550, Complainant's Response to Respondent's Petition for Commission Review of the Initial Determination, Sep. 25, 2006, pp. 1-20.
U.S. International Trade Commission, Inv. No. 337-TA-550, Complainant's Response to the OUII Petition for Commission Review of the Initial Determination, Sep. 25, 2006, p.
U.S. ITC, Inv. No. 337-TA-550, Complainant Opening Written Submission to the Commission on the Issues Under Review, Jan. 24, 2007, pp. 1-72.
U.S. ITC, Inv. No. 337-TA-550, Complainant's Response to OUII's Response to Questions Posed in the Commission's Order and Briefing, Jan. 18, 2007, pp. 1-12.
U.S. ITC, Inv. No. 337-TA-550, Complainant's Response to Respondent's Response to Notice of Commission to Review the Final Initial Determination, Jan. 18, 2007, pp. 1-45.
U.S. ITC, Inv. No. 337-TA-550, Respondent ACAMBIS PLC's Response to Notice of Commission to Review the Final Initial Determination, Jan. 22, 2007, pp. 1-42.
U.S. ITC, Inv. No. 337-TA-550, Respondent's Combined Reply to Responses to Notice of Commission to Review the Final Initial Determination, Jan. 22, 2007, pp. 1-29.
U.S. International Trade Commission, Inv. No. 337-TA-550, Notice of Commission Decision to Review the Final Initial Determination, Nov. 22, 2006, pp. 1-6.
Falconar et al., The dengue virus nonstructural-1 protein (NS1) generates antibodies to common epitopes on human blood clotting, integrin/adhesis proteins and binds to human endothelial cells: potential implications in haemorrhagic fever pathogenesis, Arch Virol 142:897-916 (1997).
Rothman et al., Multiple Specificities in the Murine CD41 and CD81 T-Cell Response to Dengue Virus, Journal of Virology 70: 6540-6546 (1996).
Shu et al., Dengue NS1-Specific Antibody Responses: Isotype Distribution and Serotyping in Patients with Dengue Fever and Dengue Hemorrhagic Fever, Jounal of Medical Virology 62:224-232 (2000).
Young et al., An Antigen Capture Enzyme-Linked Immunosorbent Assay Reveals High Levels of the Dengue Virus Protein NS1 in the Sera of Infected Patients, Journal of Clinical Microbiology 38:1053-1057 (2000).
Falconar et al., Precise location of sequential dengue virus subcomplex and complex B cell epitopes on the nonstructural-1 glycoprotein, Arch Virol 137:315-326 (1994).
Falconar et al., Production of dimer-specific and dengue virus group cross-reactive mouse monoclonal antibodies to the dengue 2 virus non-structural glycoprotein NS1, Journal of General Virology 72:961-965 (1991).
Mason et al., Sequence of the Dengue-1 Virus Genome in the Region Encoding the Three Structural Proteins and the Major Nonstructural Protein NS1, Virology 161:262-267 (1987).
"Analysis of different strains of Modified Vaccinia virus Ankara (MVA) . . . "VIVACS Final Report, Project #1200104, VIVACS GmbH, Martinsried, Germany (Jun. 29, 2005).
Falgout et al., Proper Processing of Dengue Virus Nonstructural Glycoprotein NS1 Requires the N-Terminal Hydrophobic Signal Sequence and the Downstream Nonstructural Protein NS2a, Journal of Virology 63:1852-1860 (1989).
Parrish et al., Expression of the NS1 gene of dengue virus type 2 using vaccinia virus Dimerisation of the NS1 glycoprotein, Arch Virol (1991) 117:279-286.
Pryor et al., The Effects of Site-Directed Mutagenesis on the Dimerization and Secretion of the NS1 Protein Specificed by Dengue Virus, Virology 194:769-780 (1993).
Patent Trial and Appeals Board, USPTO, Decision on Appeal U.S. Appl. No. 12/038,141, Feb. 2013.

Fig. 1A

```
2338  atgaattcacgcagcacctcactgtctgtgtcactagtattggtgggagtcgtgacgctgtatttgggagttatggtgcaggccGATAGTGGTTGCGTTGTGAGCTGGAA
   1▸ M  N  S  R  S  T  S  L  S  V  S  L  V  L  V  G  V  V  T  L  Y  L  G  V  M  V  Q  A  D  S  G  C  V  V  S  W  K
                    Signal sequence derived from E protein

2448  AAACAAAGAACTGAAGTGTGGCAGTGGGATTTTCATCACAGACAACGTGCACACATGGACAGAACAATACAAGTTCCAACCAGAATCCCCTTCAAAGCTAGCTTCAGCTA
  37▸  N  K  E  L  K  C  G  S  G  I  F  I  T  D  N  V  H  T  W  T  E  Q  Y  K  F  Q  P  E  S  P  S  K  L  A  S  A
      NS1 protein coding sequence with stop codon (TAG)

2558  TCCAGAAAGCTCATGAAGAGGGCATTTGTGGAATCCGCTCAGTAACAAGACTGGAAAATCTGATGTGGAAACAAATAACACCAGAATTGAATCACATTCTATCAGAAAAT
  74▸ I  Q  K  A  H  E  E  G  I  C  G  I  R  S  V  T  R  L  E  N  L  M  W  K  Q  I  T  P  E  L  N  H  I  L  S  E  N

2668  GAGGTGAAGTTGACTATTATGACAGGAGACATCAAAGGAATCATGCAGGCAGGAAAACGATCTCTGCAGCCCCAGCCCACTGAGCTGAAGTATTCATGGAAAACATGGGG
 111▸ E  V  K  L  T  I  M  T  G  D  I  K  G  I  M  Q  A  G  K  R  S  L  Q  P  Q  P  T  E  L  K  Y  S  W  K  T  W  G

2778  CAAAGCGAAAATGCTCTCTACAGAGTCTCATAACCAGACCTTTCTCATTGATGGCCCCGAAACAGCAGAATGCCCCAACACAAACAGAGCTTGGAATTCGCTGGAAGTTG
 147▸  K  A  K  M  L  S  T  E  S  H  N  Q  T  F  L  I  D  G  P  E  T  A  E  C  P  N  T  N  R  A  W  N  S  L  E  V

2888  AAGACTATGGCTTTGGAGTATTCACCACCAATATATGGCTAAAGTTGAGAGAAAAGCAGGATGTATTCTGCGACTCAAAACTCATGTCAGCGGCCATAAAAGACAACAGA
 184▸ E  D  Y  G  F  G  V  F  T  T  N  I  W  L  K  L  R  E  K  Q  D  V  F  C  D  S  K  L  M  S  A  A  I  K  D  N  R

2998  GCCGTCCATGCCGATATGGGTTATTGGATAGAAAGTGCACTCAATGACACATGGAAGATAGAGAAAGCCTCTTTCATCGAAGTTAAAAGCTGCCACTGGCCAAAGTCACA
 221▸  A  V  H  A  D  M  G  Y  W  I  E  S  A  L  N  D  T  W  K  I  E  K  A  S  F  I  E  V  K  S  C  H  W  P  K  S  H

3108  CACCCTCTGGAGTAATGGAGTGTTAGAAAGTGAGATGATAATTCCAAAGAATTTCGCTGGACCAGTGTCACAACACAACTACAGACCAGGCTACCATACACAAACAGCAG
 257▸  T  L  W  S  N  G  V  L  E  S  E  M  I  I  P  K  N  F  A  G  P  V  S  Q  H  N  Y  R  P  G  Y  H  T  Q  T  A

3218  GACCATGGCATCTAGGTAAGCTTGAGATGGACTTTGATTTCTGCGAAGGAACCACAGTGGTGGTGACTGAGGACTGTGGAAATAGAGGACCCTCTTTAAGAACAACTACT
 294▸ G  P  W  H  L  G  K  L  E  M  D  F  D  F  C  E  G  T  T  V  V  V  T  E  D  C  G  N  R  G  P  S  L  R  T  T  T

3328  GCCTCTGGAAAACTCATAACAGAATGGTGCTGCCGATCTTGCACATTACCACCGCTAAGATACAGAGGTGAGGACGGATGCTGGTACGGGATGGAAATCAGACCATTGAA
 331▸  A  S  G  K  L  I  T  E  W  C  C  R  S  C  T  L  P  P  L  R  Y  R  G  E  D  G  C  W  Y  G  M  E  I  R  P  L  K

3438  AGAGAAAGAAGAGAATTTGGTCAACTCCTTGGTCACAGCCtag
 367▸  E  K  E  E  N  L  V  N  S  L  V  T  A  •
```

FLAVIVIRUS NS1 SUBUNIT VACCINE

This application is a divisional of U.S. application Ser. No. 10/497,633, filed on Jun. 3, 2004, now U.S. Pat. No. 7,759, 116, which was a continuation of International Application PCT/EP02/12991, filed Nov. 20, 2002, both of which are incorporated herein by reference.

The present invention relates to NS1 proteins or parts thereof of Flaviviruses, in particular of Dengue viruses useful for vaccination against said Flavivirus and against one or more other Flaviviruses. The invention further concerns the NS1 protein or parts thereof of one Dengue virus serotype, in particular serotype 2, useful for vaccination against Dengue viruses from all serotypes. The invention further concerns DNA comprising an expression cassette coding for a Flavivirus NS1 or parts thereof, vectors comprising said DNA and vaccines containing or expressing a Flavivirus NS1.

BACKGROUND OF THE INVENTION

The etiological agent of the dengue fever is the Dengue virus, belonging to the Flavivirus genus of the family Flaviviridae (Burke and Monath, 2001). A particularly important subgroup of Flaviviruses is the group of so called mosquito-borne Flaviviruses, i.e. Flaviviruses that are transmitted by mosquitos. This group comprises in addition to the above mentioned Denguevirus other important viruses such as the West nile virus, the Japanese encephalitis virus and the Yellow fever virus (Fields Virology, ed. by Fields B. N., Lippincott-Raven Publishers, 3rd edition 1996, ISBN: 0-7817-0253-4, pages 931-1034). Typical diseases transmitted by these viruses are West nile fever and West nile encephalitis induced by the West nile virus, encephalitis induced by the Japanese encephalitis virus, Yellow fever induced by the Yellow fever virus and Dengue fever, dengue hemorrhagic fever (DHF; see below) and Dengue shock syndrome (DSS) induced by the Dengue virus.

Flaviviruses are enveloped, single-stranded, positive-sense RNA viruses formed by three structural proteins: the capsid protein (C) that forms a nucleocapsid in association with the viral genome, which is surrounded by a lipid bilayer in which are anchored the M (membrane) and E (envelope) proteins. The genome is approximately 11 kb long and contains a single open reading frame encoding a polyprotein precursor of about 3400 amino acid residues. Individual viral proteins are generated from this precursor by the action of cellular and viral proteases. The three structural proteins (C, M and E) are derived from the N-terminal part of the polyprotein and are followed by seven non-structural proteins: NS1, NS2A, NS2B, NS3, NS4A, NS4B and NS5 (Lindenbach and Rice, 2001).

Glycoprotein NS1, present in all Flaviviruses, appears to be essential for virus viability. Dengue virus NS1 is secreted from mammalian infected cells in a soluble hexameric form (Flamand et al., 1999). This noncovalently bound hexameric complex is formed by 3 dimeric subunits and has a molecular mass of 310 kDa. Dimerization is a prerequisite for NS1 protein export to the plasma membrane, where it remains as the unique viral resident protein of the infected cell surface.

In mammalian cells, but not in insect cell lines that support dengue infection, part of the transported NS1 is released into the extracellular milieu. Extracellular NS1 is secreted either as a soluble protein, which exist in a higher hexameric oligomeric form, or in association with microparticles but not with virions. In addition, NS1 has been found circulating in sera from dengue virus infected patients, suggesting that secretion of NS1 may be an important event in Flavivirus infection in the human host. During the course of a Flavivirus infection, the NS1 protein evokes a strong antibody response, which helps to clear the infecting virus from the host, presumably through a complement-mediated pathway (Schlesinger, J. J. et al., 1987) and antibody-dependant cell cytotoxicity (ADCC) (Schlesinger, J. J. et al., 1993).

The Dengue virus, with its four serotypes Dengue virus serotype 1 (Den-1) to Dengue virus serotype 4 (Den-4), is the most important member of the Flavivirus genus with respect to infections of humans and produces diseases that range from flu-like symptoms to severe or fatal illness, dengue haemorrhagic fever with shock syndrome. Dengue outbreaks continue to be a major public health problem in densely populated areas of the tropical and subtropical regions, where mosquito vectors are abundant.

The concern over the spread of dengue infection and other diseases induced by mosquito-borne Flaviviruses in many parts of the world has resulted in more efforts being made towards the development of dengue vaccines, which could prevent both dengue fever (DF), and dengue hemorrhagic fever (DHF) and in vaccines useful to protect the vaccinated individual against infections induced by some or all mosquito-borne Flaviviruses.

While most cases of DF are manifested after the first infection by any of the four serotypes, a large percentage of DHF cases occur in subjects who are infected for the second time by a serotype which is different from the first infecting serotype of dengue virus. These observations give rise to the hypothesis that sequential infection of an individual with antibody against one dengue serotype by a different virus serotype at an appropriate interval may result in DHF in a certain number of cases. Antibody-dependant enhancement (ADE) has been demonstrated in vitro for dengue viruses, as well as other enveloped viruses, and is considered to be an important mechanism in the pathogenesis of DHF.

It has also been observed that DHF usually emerges in geographic areas where multiple (three or four) virus serotypes co-circulate. In regions with endemic DHF such as Southeast Asian countries, the age-specific attack rate is higher in children, and the number of DHF cases decreases in higher age groups. This roughly corresponds with the increasing seroprevalence to dengue, indicating that natural infection may evoke protective immunity. This phenomenon is not unlike that observed with other viral infections such as hepatitis A virus. Anecdotal clinical observations have shown that patients may experience DHF twice (Nimmannitya et al., 1990) but this is rare, and it is difficult to identify accurately the serotypes causing the second and subsequent infections. So far, there has been no reports of a forth infection in the same individual, despite the fact that all four dengue virus serotypes circulate in the same area. This suggests that, in nature, infection by two or three dengue virus serotypes in the same individual may result in cross-reactive antibodies or even a cross-reactive cytotoxic lymphocyte response. This may modulate or protect against infection by the remaining dengue virus serotypes in nature.

At present there are no approved dengue vaccines. Today, prevention of dengue virus infection is dependent upon control of the principal mosquito vector, Aedes aegypti. Insecticide resistance, lack of technical and financial support that would enable local health departments to maintain effective mosquito control programs, and continuing geographic spread of both the vector mosquitoes and dengue viruses make it practically impossible to prevent dengue infections by current mosquito control programs. Therefore, development of safe and effective vaccines against all four serotypes of dengue virus has been designated by the WHO as a priority for the most cost-effective means to prevent dengue virus infection. The WHO has recommended that the ideal vaccine against dengue and DHF should be the kind that can prevent infection caused by all serotypes so that sequential infection cannot happen.

To this end WO 98/13500 proposes to use a recombinant Modified Vaccinia Virus Ankara (MVA) expressing antigens from all Dengue virus serotypes or to use four recombinant MVA wherein each of the recombinant MVA expresses at least one antigen of one Dengue virus serotype. Both strategies provide very promising strategies to vaccinate against all Dengue virus serotypes. However, it is desirable to provide a single subunit vaccine that upon administration results in an immune response against more than one Flavivirus or against more than one serotype of Dengue virus, preferably against all Dengue virus serotypes. Moreover, WO 98/13500 discloses a recombinant MVA encoding Dengue virus NS1. WO 98/13500 does not disclose that an antigen derived from one Dengue virus serotype elicits an immune response not only against the Dengue virus serotype from which the antigen is derived but also against antigens derived from other Dengue virus serotypes.

WO 99/15692 discloses a recombinant MVA containing and capable of expressing one or more DNA sequences encoding Dengue virus antigens not able to effect immune enhancement or antibody dependant enhancement. WO 99/15692 does not disclose that an antigen derived from one Dengue virus serotype elicits an immune response not only against the Dengue virus serotype from which the antigen is derived but also against antigens derived from other Dengue virus serotypes.

OBJECT OF THE INVENTION

Thus, it is an object of the invention to provide a vaccine derived from a Flavivirus or a Flavivirus serotype that is stable, can easily be produced and that leads to an immune response that protects the vaccinated individual not only against the Flavivirus or the Flavivirus serotype from which the vaccine is derived but also against other Flaviviruses or Flavivirus serotypes. It is a particular object of the present invention to provide a vaccine derived from a mosquito-borne Flavivirus that protects the vaccinated individual not only against the mosquito-borne Flavivirus or Flavivirus serotype from which the vaccine is derived but also against other mosquito-borne Flaviviruses or Flavivirus serotypes. It is a further object to provide a vaccine that is derived from one Dengue virus serotype and that protects an individual against an infection with at least two, preferably all Dengue virus serotypes.

DETAILED DESCRIPTION OF THE INVENTION

These objects have been solved using the NS1 protein or parts thereof of a Flavivirus and DNA sequences comprising an expression cassette coding for a Flavivirus NS1 protein or a part thereof, respectively. In particular, the object to provide a vaccine that is derived from one mosquito-borne Flavivirus and that protects an individual against an infection with the mosquito-borne Flavivirus from which the vaccine is derived but also against an infection with at least one other mosquito-borne Flaviviruses has been solved by using the NS1 protein or a part thereof of a mosquito-borne Flavivirus, in particular the Dengue virus, preferably Dengue virus serotype 2 and corresponding DNA sequences, respectively. More specifically the object to provide a vaccine that is derived from one Dengue virus serotype and that protects an individual at least against an infection with at least two, preferably at least three, more preferably all Dengue virus serotypes and preferably also against the infection with other Flaviviruses, in particular mosquito-borne Flaviviruses such as the Japanese encephalitis virus, the Yellow fever virus and West Nile virus has been solved by using the NS1 protein or a part thereof of a Dengue virus, in particular of Dengue virus serotype 2 and corresponding DNA sequences, respectively.

As it is shown in more detail in the experiment section the NS1 protein derived from a Dengue virus of one serotype expressed de novo after vaccination can evoke an antibody response that will cross react with NS1 proteins of Dengue virus serotype 1, 2, 3 and 4 plus NS1 from other members of the Flavivirus genus such as Japanese encephalitis virus, Yellow fever virus and West Nile virus. Thus, NS1 protein from one Dengue virus serotype origin is a universal DHF subunit vaccine for simultaneous protection against at least two, more preferably three, even more preferably all four serotypes of dengue virus and further against one or more other viruses of the genus Flavivirus. Since in this subunit vaccine strategy no E protein is involved, there should be no risk of Antibody Dependant Enhancement (ADE) upon subsequent exposure to any of the serotypes of dengue and therefore no vaccine related DHF should be induced during natural outbreaks of dengue infection.

The NS1 protein may be expressed from a nucleic acid, preferably a DNA comprising an expression cassette coding for at least a Flavivirus NS1 protein or a part thereof. The term "at least" in this context is to be interpreted in that the expression cassette may further encode additional proteins/peptides, either as separate proteins/peptides or fused to the NS1 protein or part thereof as defined in more detail below. In the context of the present invention the term "DNA" refers to any type of DNA, such a single stranded DNA, double stranded DNA, linear or circular DNA or DNA in the form of a plasmid or a viral genome. Since Flaviviruses are RNA viruses the DNA coding for the Flavivirus NS1 protein is a non-naturally occurring DNA, such as a cDNA or a synthetic DNA.

Figure 2:
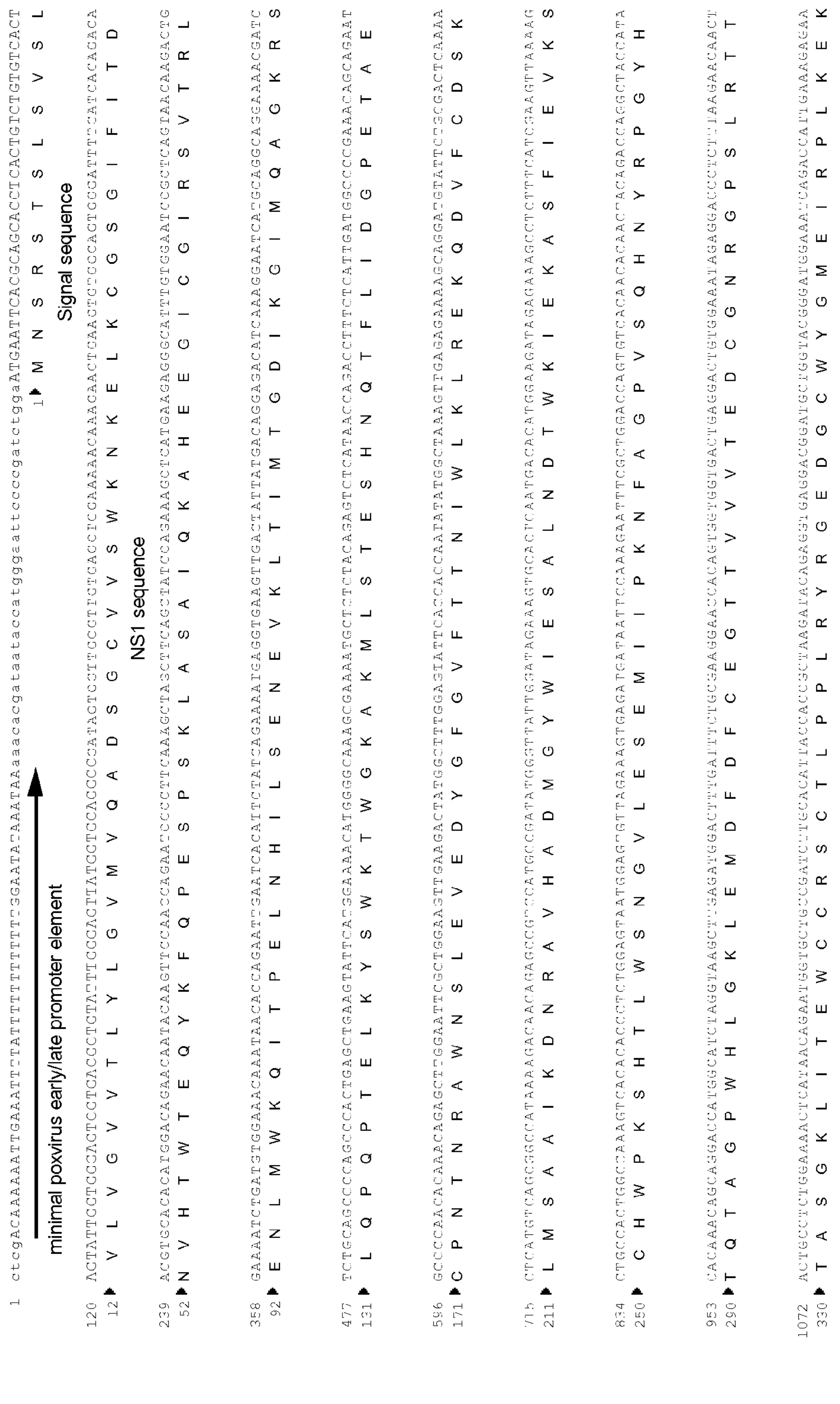

The term "expression cassette coding for a Flavivirus NS1 protein or part thereof" is to be interpreted in that the coding sequence of a Flavivirus NS1 protein or a part thereof is preceded by elements controlling the transcription, in particular the initiation of transcription. Examples for such transcriptional regulatory elements are prokaryotic promoters and eukaryotic promoter/enhancers. Preferred eukaryotic promoter/enhancers are the human Cytomegalovirus immediate early promoter/enhancer and poxvirus promoters such as the 7.5 promoter and the poxvirus minimal promoter as disclosed in the example section. The sequence of the poxvirus minimal promoter is shown in FIG. 2 as well as in SEQ:ID No. 9. The expression cassette may further contain elements controlling the termination of transcription such as prokaryotic termination elements or eukaryotic poly A signal sequences, if necessary.

The expression cassette may express only the NS1 protein or part thereof of a Flavivirus or may express the NS1 protein or part thereof together with one or more further Flavivirus proteins/peptides, wherein the NS1 protein or part thereof and the further proteins/peptides are produced as separate proteins/peptides or as fusion proteins/peptides. If not defined otherwise in this description the term "peptide" in the context of the present invention refers to a contiguous amino acid sequence stretch of at least 10 amino acids, more preferably of at least 20 amino acids, most preferably of at least 25 amino acids.

The further Flavivirus protein is not the entire E-protein since this protein seems to be involved in the development of DHF. Thus, if the further Flavivirus peptide is derived from the E-protein it should comprise less than 40 amino acids, preferably less than 35 amino acids. If amino acid sequence stretches derived from the E-protein are expressed together with the NS1 protein or part thereof it should have been verified that this amino acid stretch does not comprise an epitope that is involved in the generation of ADE and DHF.

If the expression cassette expresses in addition to the NS1 protein or part thereof a further Flavivirus protein/peptide as separate proteins/peptides the expression cassette may comprise an Internal ribosome entry site (IRES) between the sequence encoding the NS1 protein or part thereof and the sequence encoding the further Flavivirus protein. IRES elements are known to the person skilled in the art. Examples for IRES elements are the picornaviral IRES elements or the 5"non-coding region of the hepatitis C virus.

Alternatively the nucleotide sequence encoding the NS1 protein or part thereof may be fused to a DNA sequence encoding further Flavivirus proteins/peptides in such a way that a fusion protein between the NS1 protein or part thereof and the further Flavivirus protein/peptide is produced. If the NS1 protein or part thereof and the further Flavivirus protein/peptide are to be produced as fusion proteins/peptides the respective coding sequences are fused in frame.

In a preferred embodiment the DNA sequence encoding the NS1 protein or part thereof is preceded by the sequence encoding the glycosylation signal sequence of the E-protein. According to this embodiment a fusion protein is produced that comprises the E-protein gylcosylation signal sequence fused to the NS1 protein or part thereof. As pointed out above the E-protein derived amino acid stretch should be as short as possible and it should be excluded that this amino acid stretch contains an epitope involved in the generation of ADE and DHF. The gylcosylation signal sequence of the E-protein fulfils these requirements.

In an alternative preferred embodiment the expression cassette used according to the present invention contains as only Flavivirus sequence the sequence encoding the NS1 protein or part thereof. Thus, in this preferred embodiment the expression cassette according to the present invention does not express any other peptides/proteins from other parts of the Flavivirus genome, in particular not the NS2A or the E protein.

In a further alternative embodiment the DNA according to the present invention expresses the NS1 protein or part thereof as a fusion protein with proteins/peptides that are not derived from a flavivirus. Such proteins/peptides comprise non-flaviviral signal sequences or sequences that are useful for the detection or purification of the expressed fusion protein, such as tags.

To understand the general structure of the Flavivirus sequence in the expression cassette used according to a preferred embodiment of the present invention it is helpful to summarize briefly the genome structure of Flaviviruses: During a natural Flavivirus infection the virus produces a single polyprotein which is then cleaved first by host cell proteases and then virus encoded proteases into the following proteins: C, PrM and M, E, NS1, NS2A, NS2B, NS3, NS4A, NS4B and NS5 (protein order along the polyprotein precursor). Therefore, a DNA sequence, in particular a cDNA sequence coding for the NS1 protein or part thereof must require the addition of a "ATG" start codon. In a preferred embodiment the start ATG is then followed by a sequence encoding a glycosylation signal so that the newly synthesized NS1 protein becomes glycosylated in the endoplasmic reticulum. Such signal sequences are known to the person skilled in the art. Finally, the protein-coding cassette needs a stop codon, which might be a TAG added to the 3' terminal end of the protein coding cDNA sequence. In the example used in this invention the "ATG+signal sequence" element was derived from the sequence encoding the hydrophobic C-terminal end of the E protein (the last 28 amino acids, which for the Dengue virus New Guinea strain ("NGC strain", GeneBank accession number AF038403) starts with the amino acid M (ATG). A typical expression cassette according to the present invention is shown in FIG. 2 and as SEQ:ID No 9 and SEQ:ID No. 10.

Figure 1C:
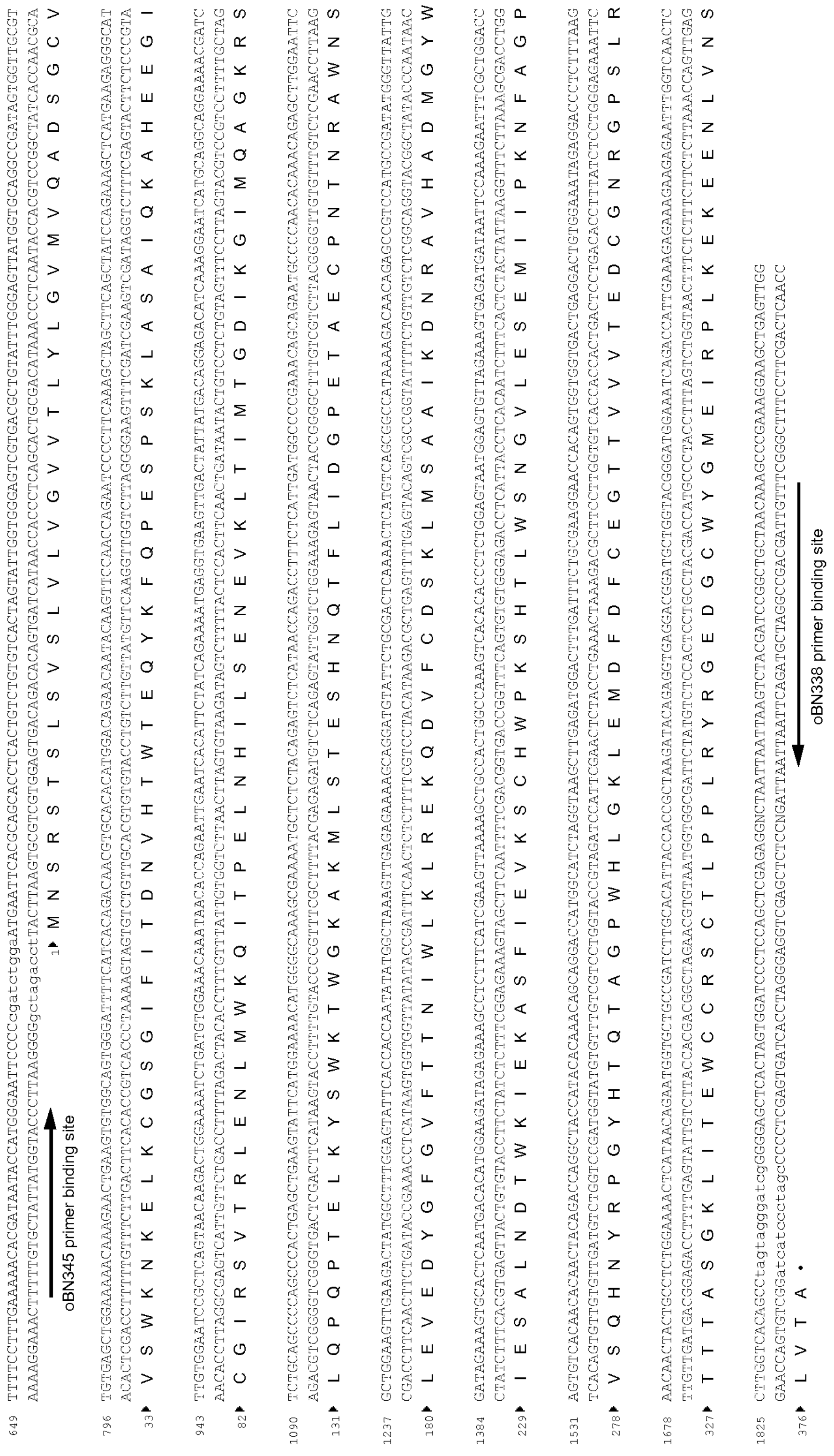

Thus, in summary this embodiment concerns the use of a DNA comprising an expression cassette comprising the sequences coding for a Flavivirus NS1 protein or part thereof, wherein the coding sequence is preceded by a start codon ("ATG") and a sequence encoding a signal sequence for glycosylation, preferably derived from the E-protein as defined above and wherein the coding sequence is terminated by a stop codon of translation (FIGS. 1A, 1C and 2, SEQ:ID 5-10).

The DNA sequence that may be used according to the present invention encodes a Flavivirus NS1 protein or part thereof. The term "Flavivirus" refers to any Flavivirus. More preferably the term "Flavivirus" refers to mosquito-borne Flaviviruses such as the West nile virus, the Japanese encephalitis virus, the Yellow fever virus and the Dengue virus. The NS1 protein or part thereof derived from one mosquito-borne virus encoded by a DNA according to the present invention should protect the vaccinated individual not only against an infection with the virus or virus serotype from which the vaccine is derived but also against the infection with other mosquito-borne viruses or other serotypes of the virus from which the vaccine is derived. The NS1 protein can preferably be of any Dengue virus serotype. More preferably the NS1 protein coding sequence is derived from a Dengue virus serotype 2 such as the Dengue virus New Guinea strain ("NGC strain", GeneBank accession number AF038403). The terms "subtype" and "serotype" are used interchangeably throughout this description.

The term "part thereof" in the context of the term "NS1 protein or part thereof" refers to an amino acid stretch of the NS1 protein, which is sufficiently long to induce a specific immune response against the NS1 protein from which the "part thereof" is derived. If the Flavivirus is a Dengue virus the amino acid stretch should be an amino acid stretch that provokes an immune response in a vaccinated animal including a human against the NS1 proteins of all Dengue virus serotypes. In the examples section it is shown how the person skilled in the art can determine whether an NS1 protein or part thereof induces an immune response specific for all Dengue virus serotypes. According to a preferred embodiment the Flavivirus DNA sequence encodes the entire NS1 protein. Thus, the term "NS1 protein or part thereof" relates to the entire sequence of naturally occurring NS1 proteins and shorter eptitope stretches that still elicit an immune response.

Moreover the term "NS1 protein" also relates to derivatives of naturally occurring NS1 proteins. Such a derivative may be a protein that has one or more amino acid substitutions, deletions and/or insertion with respect to the naturally occurring NS1 protein. By way of example such a derivative is a protein that has a homology in the amino acid sequence of at least 50%, preferably of at least 75%, more preferably of at least 90%. Consequently, the term "part thereof" also relates to parts of such a NS1 protein derivative.

In summary one of the most preferred embodiments of the present invention is to use a DNA comprising an expression cassette coding for a mosquito-borne Flavivirus NS1 or part thereof, wherein the Flavivirus is preferably the Dengue virus, in particular Dengue virus serotype 2, and wherein the expression of the NS1 protein or part thereof is controlled by a transcriptional regulatory element. More preferably the DNA according to the present invention encodes the NS1 protein or part thereof as a fusion protein with a glycosylation signal sequence.

The invention further refers to vectors comprising a DNA as described above and to the use of said vectors to induce an immune response according to the present invention. The term "vector" refers to any vectors known to the person skilled in the art. A vector can be a plasmid vector such as pBR322 or a vector of the pUC series. More preferably the vector is a virus vector. In the context of the present invention the term "viral vector" or "virus vector" refers to an infectious virus comprising a viral genome. In this case the DNA of the present invention is to be cloned into the viral genome of the respective viral vector. The recombinant viral genome is then packaged and the thus obtained recombinant vectors can be used for the infection of cells and cell lines, in particular for the infection of living animals including humans. Typical virus vectors that may be used according to the present invention are adenoviral vectors, retroviral vectors or vectors on the basis of the adeno associated virus 2 (AAV2). Most preferred are poxviral vectors. The poxvirus may be preferably a canarypox virus, a fowlpoxvirus or a vaccinia virus. More preferred is modified vaccinia virus Ankara (MVA) (Sutter, G. et al. [1994], Vaccine 12: 1032-40). A typical MVA strain is MVA 575 that has been deposited at the European Collection of Animal Cell Cultures under the deposition number ECACC V00120707. Most preferred is MVA-BN or a derivative thereof which has been described in the PCT application WO 02/42480 (PCT/EP01/13628). The content of this application is included in the present application by reference. MVA-BN has been deposited at the European Collection of Animal Cell Cultures with the deposition number ECACC V00083008. By using MVA-BN or a derivative thereof the additional technical problem has been solved to provide a particular safe virus vaccine against Flaviviruses since it has been shown that the MVA-BN virus vector is an extremely attenuated virus. In particular, it has been demonstrated that MVA-BN is more attenuated than the MVA strains known before in the prior art. MVA-BN is derived from Modified Vaccinia Ankara virus and is characterized by the loss of its capability to reproductively replicate in human cell lines. MVA-BN is safer than any other known vaccinia virus strains due to a lack of replication in humans. In the preferred embodiment the invention concerns as a viral vector containing the DNA as defined above MVA-BN and derivatives of MVA-BN. The features of MVA-BN, the description of biological assays allowing to evaluate whether a MVA strain is MVA-BN or a derivative thereof and methods allowing to obtain MVA-BN or a derivative thereof are disclosed in WO 02/42480.

The term "derivatives" of the virus as deposited under ECACC V00083008, i.e. derivatives of MVA-BN, is used in the present application as defined in WO 02/42480. In the following the features of a derivative of MVA-BN are shortly summarized. For more detailed information regarding the definition of a derivative of MVA-BN and in particular for detailed information regarding the biological assays used to determine whether a MVA virus is a derivative of MVA-BN reference is made to WO 02/42480. Thus, said term refers to vaccinia viruses showing at least one of the following features of the deposited strain MVA-BN but showing differences in one or more parts of its genome. Preferably a derivative has at least two, more preferably at least three, most preferably all of the following four features of MVA-BN:

- capability of reproductive replication in chicken embryo fibroblasts (CEF) and in the baby hamster kidney cell line BHK (ECACC 85011433), but no capability of reproductive replication in the human cell line HaCat (Boukamp et al. 1988, J Cell Biol. 106(3): 761-71),
- failure to replicate in vivo,
- induction of a higher immunogenicity compared to the known strain MVA 575 (ECACC V00120707) in a lethal challenge model and/or
- induction of at least substantially the same level of immunity in vaccinia virus prime/vaccinia virus boost regimes when compared to DNA-prime/vaccinia virus boost regimes.

In particular a derivative of MVA-BN has essentially the same replication characteristics than MVA-BN. Viruses having the same "replication characteristics" than the deposited virus are viruses that replicate with similar amplification ratios than the deposited strain in CEF cells and the cell lines BHK, HeLa, HaCat and 143B and that show a similar replication in vivo as determined in the AGR129 transgenic mouse model.

The term "not capable of reproductive replication" is used in the present application as defined in WO 02/42480. Thus, a virus that is "not capable of reproductive replication" is a virus that shows an amplification ratio of less than 1 in the human cell line HaCat (Boukamp et al. 1988, J Cell Biol. 106(3): 761-71. Preferably, the amplification rate of the virus used as a vector according to the invention is 0.8 or less in the human cell line HaCat. The "amplification ratio" of a virus is the ratio of virus produced from an infected cell (Output) to the amount originally used to infect the cells in the first place (Input) ("amplification ratio"). A ratio of "1" between Output and Input defines an amplification status wherein the amount of virus produced from the infected cells is the same as the amount initially used to infect the cells.

In the context of the definition of MVA-BN and its derivatives the term "failure to replicate in vivo" is used in the present application as defined in WO 02/42480. Thus, said term refers to viruses that do not replicate in humans and in the mice model as explained in WO 02/42480. The mice used in WO 02/42480 are incapable of producing mature B- and T-cells (AGR 129 mice). In particular MVA-BN and its derivatives do not kill AGR129 mice within a time period of at least 45 days, more preferably within at least 60 days, most preferably within 90 days after the infection of the mice with $10^7$ pfu virus administered intra peritonealy. Preferably, the viruses that show "failure to replicate in vivo" are further characterized in that no virus can be recovered from organs or tissues of the AGR129 mice 45 days, preferably 60 days and most preferably 90 days after the infection of the mice with $10^7$ pfu virus administered intra peritonealy.

MVA-BN and its derivatives are preferably characterized by a higher immunogenicity compared to the known strain MVA 575 as determined in a lethal challenge mouse model as explained in WO 02/42480. In such a model unvaccinated mice die after the infection with replication competent vaccinia strains such as the Western Reserve strain L929 TK+ or IHD-J. The infection with replication competent vaccinia viruses is referred to as "challenge" in the context of description of the lethal challenge model. Four days after the challenge the mice are usually killed and the viral titer in the ovaries is determined by standard plaque assays using VERO cells. The viral titer is determined for unvaccinated mice and for mice vaccinated with MVA-BN and its derivatives. More specifically MVA-BN and its derivatives are characterized in that in this test after the vaccination with $10^2$ $TCID_{50}$/ml virus the ovary virus titers are reduced by at least 70%, preferably by at least 80%, more preferably by at least 90% compared to unvaccinated mice.

MVA-BN or its derivatives are preferably characterized by inducing at least substantially the same level of immunity in vaccinia virus prime/vaccinia virus boost regimes when compared to DNA-prime/vaccinia virus boost regimes. A vaccinia virus is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably the CTL response after vaccinia virus prime/vaccinia virus boost administration is higher in at least one of the assays, when compared to DNA-prime/vaccinia virus boost regimes. Most preferably the CTL response is higher in both assays.

WO 02/42480 discloses how Vaccinia viruses are obtained having the properties of MVA-BN and its derivatives as defined above.

Methods to insert the DNA as defined above into poxviral DNA and methods to obtain recombinant poxviruses are known to the person skilled in the art. In a recombinant vaccinia virus the expression of the DNA according to the present invention is preferably, but not exclusively, under the transcriptional control of a poxvirus promoter, more preferably of a vaccinia virus promoter. The insertion of the DNA according to the present invention is preferably into a non-essential region of the virus genome. In another preferred embodiment of the invention, the heterologous nucleic acid sequence is inserted at a naturally occurring deletion site of the MVA genome (disclosed in PCT/EP96/02926).

In summary it is one of the most preferred embodiments of the present invention to provide a vector comprising the DNA as defined above, wherein the vector is MVA-BN or a derivative thereof and wherein the DNA comprises an expression cassette coding for a Flavivirus NS1 protein or part thereof, wherein the Flavivirus is preferably a Dengue virus, more preferably Dengue virus serotype 2.

In a preferred embodiment the invention relates to the usefulness of the NS1 protein or part thereof encoded by a DNA according to the present invention or by a vector according to the present invention for vaccination against several flaviviruses or flavivirus serotypes. For the definition of the NS1 protein or part thereof according to the present invention reference is made to the above parts of the description where the DNA encoding NS1 has been defined by the product expressed from said DNA. The following summary regarding the protein according to the present invention is therefore not to be regarded as a limitation of the invention. In summary the NS1 protein can be an isolated NS1 protein or part thereof encoded by any Flavivirus. The NS1 protein or part thereof is preferably derived from a Dengue virus, most preferably from Dengue virus serotype 2. The protein may only comprise the amino acid sequence of a viral NS1 protein or part thereof. In a preferred embodiment the NS1 protein may contain additional amino acids that are required for an effective expression of the protein. Examples for such amino acids/amino acid sequences are shown above and include the methionine at the N-terminus of the protein encoded by an added ATG codon and an amino acid sequence derived from the C-terminal end of the E-protein acting as a signal sequence for glycosylation of the NS1 protein or part thereof. Other signal sequences are also within the scope of the present invention. In an alternative embodiment the NS1 amino acid sequence or a part thereof can be fused to other proteins/peptides. Examples for fusion partners are sequences allowing the identification of the protein such as tags or other flaviviral proteins or parts thereof.

In a preferred embodiment the present invention concerns the DNA, the vector or the NS1 protein or part thereof according to the present invention as a vaccine, in particular as a vaccine against several flaviviruses or flavivirus serotypes. A "vaccine" is a compound, i.e. a DNA, a protein, a vector or a virus that induces a specific immune response.

According to one alternative of this embodiment the "vaccine" according to the present invention is based on a Dengue virus NS1 protein or a part thereof which induces an immune response against the NS1 proteins of all Dengue virus serotypes. In particular it has been shown that the NS1 protein of one Dengue virus serotype, in particular serotype 2, induces an immune response against the NS1 proteins of at least two, preferably at least three, most preferably all Dengue virus serotypes and preferably also against at least one other mosquito-borne Flavivirus.

As explained above the inventors of the present invention have found that the NS1 protein or part thereof according to the present invention of one Flavivirus induces an immune response against the NS1 protein of other Flaviviruses. As pointed out above the "Flavivirus" is preferably a mosquito-borne Flavivirus. In other words the inventors of the present invention have found that in an alternative embodiment the NS1 protein or part thereof according to the present invention of one mosquito-borne Flavivirus induces an immune response against the NS1 protein of the mosquito-borne Flavivirus from which the vaccine is derived and also against other mosquito-borne Flaviviruses. Thus, the vaccine derived from a mosquito-borne Flavivirus is useful as vaccine against one or more mosquito-borne flaviviruses. The term "vector derived from a Flavivirus" or similar terms in the context of the present description means that a vector as defined above (e.g. a poxvirus vector or a plasmid) contains a DNA as defined above. Thus, this term refers to the vector insert and not the vector backbone. An example for a "vector derived from a Flavivirus" is a poxvirus vector, such as MVA, comprising an expression cassette comprising a poxvirus promoter, a sequence encoding a Flavivirus NS1 protein or part thereof, wherein the sequence coding for the Flavivirus NS1 protein or part thereof is preceded by an ATG codon and a sequence encoding a glycosylation signal sequence and wherein the coding sequence is terminated by a stop codon of translation.

Thus the vaccination with the DNA, the vector or the NS1 protein or part thereof is useful as a single subunit vaccine against a broad range of Flaviviruses or at least Flavivirus serotypes. The DNA or vector encoding the NS1 protein or part thereof from one Flavivirus or Flavivirus serotype or the NS 1 protein or part thereof from said Flavivirus or serotype can thus be used as a vaccine for vaccination against other Flaviviruses and Flavivirus serotypes, respectively. For example a vaccine derived from a Dengue virus serotype 2 can be used as a vaccine against one, two or all of the serotypes 1, 3 and 4, as well as vaccine against serotype 2. It may further be useful to protect an individual against other Flaviviruses such as the West Nile Virus, the Japanese encephalitis virus and the Yellow fever virus.

In a preferred embodiment the DNA according to the present invention is used as a vaccine. It is known by the person skilled in the art that the administration of naked DNA harboring a eukaryotic expression cassette as in the present invention, in particular the intramuscular injection of DNA leads to the expression of the protein encoded by the expression cassette. The protein is exposed to the immune system and a specific immune response is raised.

In an alternative embodiment the vaccination is made by administering a vector according to the present invention, in particular a viral vector, more preferably a poxvirus vector, most preferably a vaccinia virus vector, e.g. a MVA vector.

For the preparation of vaccinia virus based vaccine, the virus according to the invention, in particular MVA-BN and its derivatives, is converted into a physiologically acceptable form. This can be done based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titer of $5\times10^8$ $TCID_{50}$/ml formulated in about 10 mM Tris, 140 mM NaCl pH 7.4. For the preparation of vaccine shots, e.g., $10^2$-$10^9$ particles of the virus are lyophilized in 100 ml of phosphate-buffered saline (PBS) in the presence of 2% peptone and 1% human albumin in an ampoule, preferably a glass ampoule.

It is particularly preferred that the vaccinia virus based vaccine, in particular a MVA-BN based vaccine, used for vaccination is stored in a freeze-dried state. It is shown in the example section that the immune reaction as well as the percentage of cross reaction of the immune response induced by the NS1 protein of one flavivirus to the NS1 protein of different flaviviruses and flavivirus serotypes, respectively, is particularly high if the virus used for vaccination was stored as freeze dried virus. Thus, the vaccine shots preferably can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. An typical virus containing formulation suitable for freeze-drying comprises 10 mM Tris-buffer, 140 mM NaCl, 18.9 g/l Dextran (MW 36000-40000), 45 g/l Sucrose, 0.108 g/l L-glutamic acid mono potassium salt monohydrate pH 7.4. After freeze-drying the glass ampoule is then sealed and can be stored between 4° C. and room temperature for several months. However, as long as no need exists the ampoule is stored preferably at temperatures below −20° C. For vaccination the lyophilisate can be dissolved in 0.1 to 0.5 ml of an aqueous solution, such a water, physiological saline or Tris buffer, and administered either systemically or locally, i.e. by parenterally, intramuscularly or any other path of administration know to the skilled practitioner. The mode of administration, the dose and the number of administrations can be optimized by those skilled in the art in a known manner. Most preferred for poxvirus vectors is subcutaneous or intramuscular administration. Most preferably the vaccination is done by administration of two vaccine shots in an interval of e.g. 3 to 5 weeks.

If the vaccine is a MVA-BN vector or derivative thereof comprising a DNA according to the present invention a particular embodiment of the present invention concerns a kit for vaccination comprising a MVA-BN virus vector according to the present invention for the first vaccination (“priming”) in a first vial/container and for a second vaccination (“boosting”) in a second vial/container.

If the vaccine is a MVA-BN vector or derivative thereof comprising a DNA as defined above a particular embodiment of the present invention concerns the administration of the vaccine in therapeutically effective amounts in a first inoculation (“priming inoculation”) and in a second inoculation (“boosting inoculation”). The interval between the priming inoculation and the boosting inoculation is e.g. 2 to 12 weeks, preferably e.g. 3-6 weeks, more preferably e.g. about 3 weeks. The virus amount used for vaccination shout be at least $1\times10^2$ $TCID_{50}$, preferably e.g. $1\times10^7$ $TCID_{50}$ to $1\times10^9$ $TCID_{50}$. Moreover, a particular embodiment of the present invention concerns a kit for vaccination comprising a MVA-BN virus vector as defined above for the first vaccination (“priming”) in a first vial/container and for a second vaccination (“boosting”) in a second vial/container.

Thus, the invention concerns in the vaccine embodiments a vaccine comprising a DNA, a vector or a NS1 protein or part thereof as defined above and the use of said DNA, vector or protein for the preparation of a vaccine. According to a preferred embodiment the invention concerns the use of said DNA, vector or protein for the preparation of a vaccine wherein the NS1 protein or part thereof, the NS1 protein or part thereof encoded by the DNA or the vector is from one Dengue virus serotype and wherein the DNA, the vector or the NS1 protein or part thereof is used as a vaccine against two, three or all Dengue virus serotypes. Most preferably the Dengue virus serotype is serotype 2.

The invention further relates to a method for the treatment or prevention of a Flavivirus infection comprising inoculating an animal, including a human, in need thereof with a DNA as above, a vector as above or a NS1 protein or part thereof as above. In particular the invention relates to a method as above, wherein the NS1 protein or part thereof or the NS1 protein or part thereof encoded by the DNA or the vector is from one Dengue virus serotype and wherein the DNA, the vector or the NS1 protein or part thereof is used as a vaccine against two, three or all Dengue virus serotypes

SUMMARY OF THE INVENTION

The invention relates in particular to the following, alone or in combination:

Use of

- a nucleic acid comprising an expression cassette comprising a transcriptional regulatory element and a sequence which codes at least for the NS1 protein or a part thereof of a mosquito-born flavivirus,
- a vector comprising said nucleic acid and/or
- a NS1 protein or part thereof of said flavivirus for the preparation of a vaccine against the mosquito-borne Flavivirus from which the nucleic acid or the NS1 protein or part thereof is derived and against at least one other mosquito-borne Flavivirus.

Use as above, wherein the mosquito-born Flavivirus from which the nucleic acid or the NS1 protein or part thereof is derived is a Dengue virus.

Use of a

- nucleic acid comprising an expression cassette comprising a transcriptional regulatory element and a sequence which codes at least for the NS1 protein or a part thereof of a Dengue virus serotype,
- vector comprising said nucleic acid and/or
- NS1 protein or part thereof of said Dengue virus serotype for the preparation of a vaccine against all Dengue virus serotypes and optionally against at least one other mosquito-borne Flavivirus.

Use as above, wherein the Dengue virus from which the nucleic acid or the NS1 protein or part thereof is derived is Dengue virus serotype 2.

Use as above, wherein the sequence coding for the NS1 protein or part thereof of the mosquito-borne flavivirus or of the Dengue virus serotype is preceded by an ATG codon and a sequence encoding a glycosylation signal sequence and wherein the coding sequence is terminated by a stop codon of translation.

Use as above, wherein the other mosquito-borne Flavivirus is selected from the West Nile virus, the Yellow fever virus and the Japanese Enzephalitis virus.

Use as above, wherein the vector is a poxvirus vector.

Use as above, wherein the poxvirus vector is a Modified Vaccinia Virus Ankara (MVA) strain, in particular MVA-BN deposited at the European Collection of Cell Cultures under number V00083008 or a derivative thereof.

Use as above, wherein the poxvirus vector is freeze-dried and is reconstituted in a pharmaceutically acceptable diluent prior to administration.

Use as above, wherein the transcriptional regulatory element is a poxvirus promoter.

Use as above, wherein the vaccine is administered in therapeutically effective amounts in a first inoculation ("priming inoculation") and in a second inoculation ("boosting inoculation")

Method for the treatment or prevention of a flavivirus infections comprising inoculating an animal, including a human, in need thereof with

- a nucleic acid comprising an expression cassette comprising a transcriptional regulatory element and a sequence which codes at least for the NS1 protein or a part thereof of a mosquito-born flavivirus,
- a vector comprising said nucleic acid and/or
- a NS1 protein or part of said flavivirus, wherein the Flavivirus infection is an infection by the mosquito-borne Flavivirus from which the nucleic acid, or the NS1 protein or part thereof is derived and/or an infection by another mosquito-borne Flavivirus.

Method as above, wherein the mosquito-borne Flavivirus from which the nucleic acid or NS1 protein or part thereof is derived is a Dengue virus.

Method for the treatment or prevention of a Flavivirus infection comprising inoculating an animal, including a human, in need thereof with

- a nucleic acid comprising an expression cassette comprising a transcriptional regulatory element and a sequence which codes at least for the NS1 protein or a part thereof of a Dengue virus serotype,
- a vector comprising said nucleic acid and/or
- a NS1 protein or part thereof of said Dengue virus serotype, wherein the Flavivirus infection is an infection by the Dengue virus serotype from which the nucleic acid, or the NS1 protein or part thereof is derived and/or an infection by another Dengue virus serotypes and/or an infection by other mosquito-borne Flaviviruses.

Method as above, wherein the Dengue virus from which the DNA or the protein or part thereof is derived is Dengue virus serotype 2.

Method as above, wherein the sequence coding for the NS1 protein or part thereof of the mosquito-borne flavivirus or of the Dengue virus serotype is preceded by an ATG codon and a sequence encoding a glycosylation signal sequence and wherein the coding sequence is terminated by a stop codon of translation.

Method as above, wherein the vector is a poxvirus vector.

Method as above, wherein the poxvirus vector is a Modified Vaccinia Virus Ankara (MVA) strain Method as above, wherein the MVA strain is MVA-BN deposited at the European Collection of Cell Cultures under number V00083008 or a derivative thereof.

Method as above, wherein the poxvirus vector is freeze-dried and is reconstituted in a pharmaceutically acceptable diluent prior to administration.

Method as above, wherein the transcriptional regulatory element is a poxvirus promoter.

Method as above, wherein the poxvirus vector or the pharmaceutical composition is administered in therapeutically effective amounts in a first inoculation ("priming inoculation") and in a second inoculation ("boosting inoculation")

Poxvirus vector harboring a DNA comprising an expression cassette comprising a transcriptional regulatory element and a sequence which codes at least for a Flavivirus NS1 protein or a part thereof, wherein the poxvirus is Modified Vaccinia Virus Ankara (MVA) strain BN deposited at the European Collection of Cell Cultures under number V00083008 or a derivative thereof.

Poxvirus vector as above, wherein the Flavivirus is a mosquito-borne Flavivirus, in particular a Dengue virus.

Poxvirus vector as above, wherein the Dengue virus is Dengue virus serotype 2.

Poxvirus vector as above, wherein the sequence coding for the Flavivirus NS1 protein or part thereof is preceded by an ATG codon and a sequence encoding a glycosylation signal sequence and wherein the coding sequence is terminated by a stop codon of translation.

Poxvirus vector as above, wherein the transcriptional regulatory element is a poxvirus promoter.

Poxvirus vector as above, wherein the poxvirus vector is freeze-dried.

Poxvirus vector as above as a vaccine.

Pharmaceutical composition comprising a poxvirus vector as above and a pharmaceutically acceptable carrier, diluent and/or additive.

Poxvirus vector as above or pharmaceutical composition as above for the treatment and/or prevention of a flavivirus infection, wherein the poxvirus vector or the pharmaceutical composition is administered in therapeutically effective amounts in a first inoculation ("priming inoculation") and in a second inoculation ("boosting inoculation")

Method for the treatment or prevention of a flavivirus infection comprising inoculating an animal, including a human, in need thereof with a vector as above or with the pharmaceutical composition as above.

Cell, preferably a human cell, comprising a poxvirus vector as above.

Use of the poxvirus vector as above for the preparation of a vaccine to treat or to prevent a Flavivirus infection.

Kit for prime/boost immunization comprising a poxvirus vector as above or a pharmaceutical composition as above for a first inoculation ("priming inoculation") in a first vial/container and for a second inoculation ("boosting inoculation") in a second vial/container.

SHORT DESCRIPTION OF THE FIGURES

FIG. 1A: The dengue NGC strain "signal sequence+NS1" cDNA protein coding sequence of the construct used as an example in this invention. The start of the NS1 gene in the natural context is indicated by an arrow. Important features are the addition of an ATG start codon and a stop codon (in this example "TAG"). Nucleotide sequence numbers refer to position in the NGC strain genome (Genbank accession number AF038403). The nucleotide and amino acid sequence in FIG. 1A corresponds to SEQ:ID No. 5. The amino acid is separately shown as SEQ:ID No. 6.

FIG. 1B: Diagram of plasmid pAF7NS1 containing the dengue NGC strain "signal sequence+NS1" protein coding sequence.

FIG. 1C: Nucleotide sequence of the NS1 cassette within plasmid pAF7 showing the primer binding sites for PCR amplification of this cassette with oBN345 and oBN338. The nucleotide and amino acid sequence in FIG. 1C corresponds to SEQ:ID No. 7. The amino acid is separately shown as SEQ:ID No. 8.

Figure 1D:
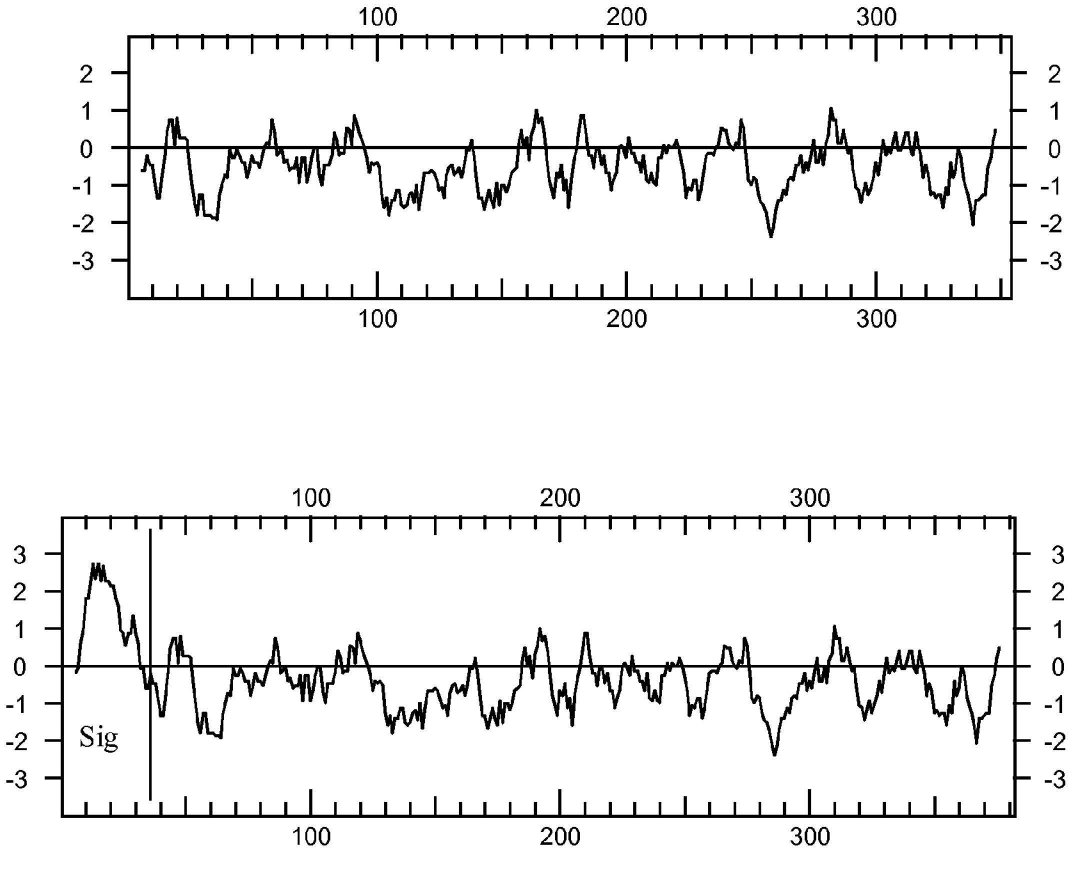

FIG. 1D: top: Kyte-Doolittle hydrophicity plot of dengue NGC strain NS1 amino acid sequence (amino acid 776 to 1127 of dengue NCG polyprotein Genbank Accession AF038403). Values above zero=hydrophobic. bottom: Kyte-Doolittle hydrophicity plot of dengue NGC strain NS1 amino acid sequence containing a signal sequence derived from the last 28 amino acids of C-terminal of E protein (amino acid 748 to 775). The total amino acid sequence represents amino acid 748 to 1127 of the dengue NCG polyprotein (Genbank Accession AF038403) which for this strain starts with an "ATG" start codon but lacks a stop codon. Sig=Signal sequence. Values above zero=hydrophobic FIG. 2: Nucleotide sequence of the "poxvirus promoter+signal sequence+NS1" expression cassette. The nucleotide and amino acid sequence in FIG. 2 corresponds to SEQ:ID No. 9. The amino acid is separately shown as SEQ:ID No. 10. Briefly, the minimal poxvirus early/late promoter element controls the expression of the NS1 protein of Dengue virus serotype 2, wherein the N-terminus of the NS1 protein is fused to the 28 C-terminal aminoacids of the E-protein. The translation is terminated at an TAG stop codon that has been inserted into the nucleic acid sequence.

Figure 3A:
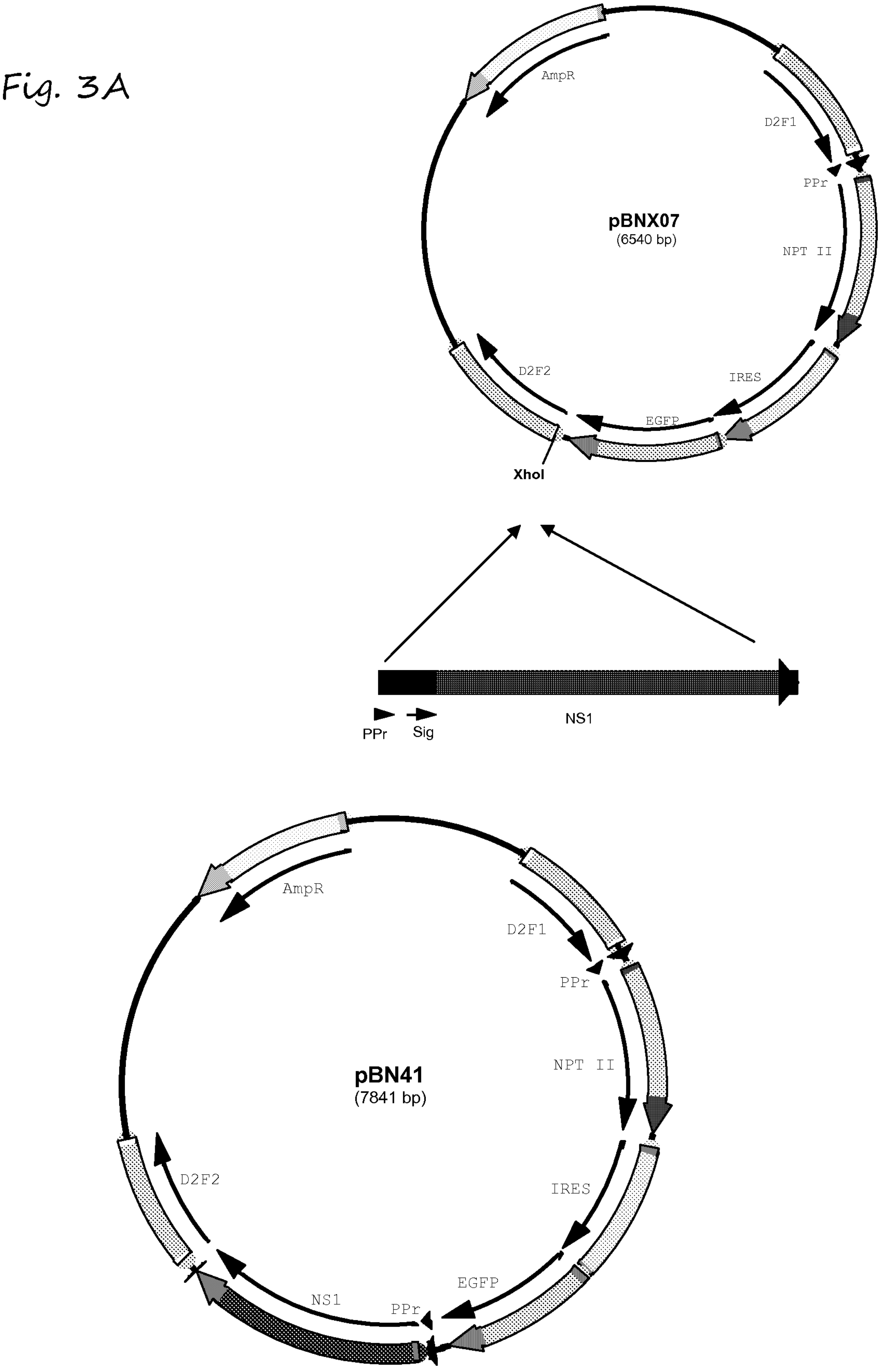

FIG. 3A: Cloning of NS1 expression cassette into the blunt ended Xho I site (blunt end cloning) of pBNX07 to produce the clone pBN41. PPr=poxvirus promoter, D2F1=flank 1 of deletion site 2, NPT II=neomycin resistance gene, IRES=Internal Ribosome Binding Site, EGFP=Enhanced Green Fluorescence Protein, NS1 (in pBN41)=signal sequence+NS1, D2F2=Flank 2 of deletion site 2, Sig=signal sequence. AmpR=Ampicillin resistance gene.

Figure 3B:
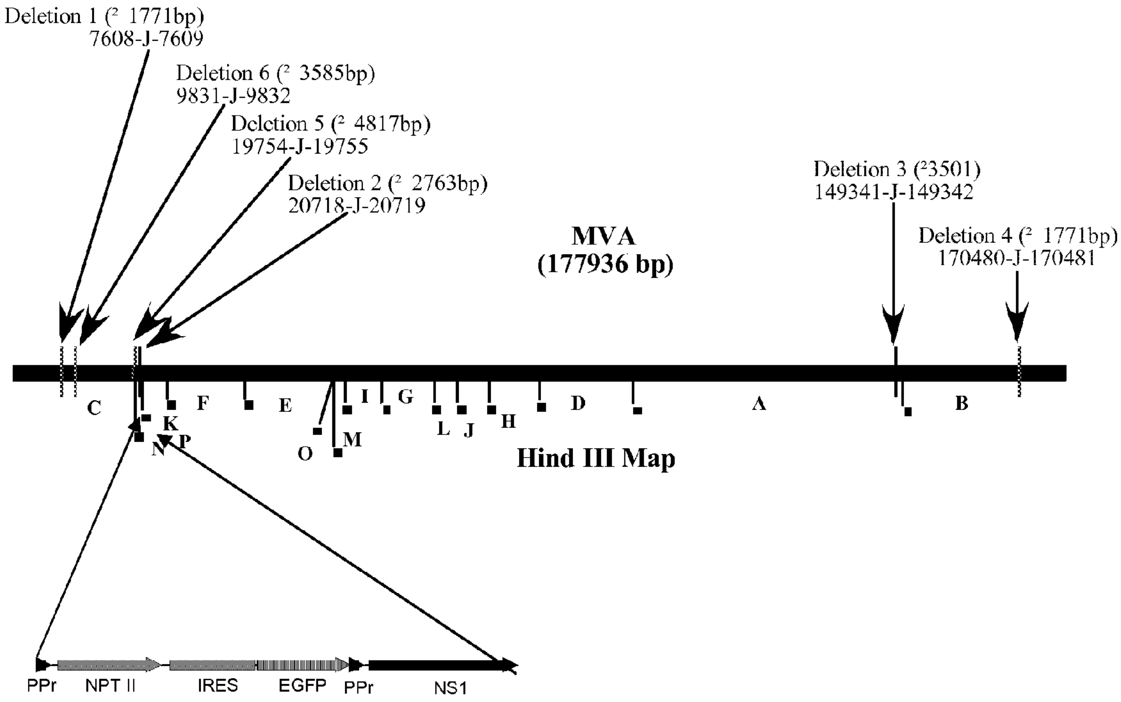

FIG. 3B: Hind III map of MVA (Genbank U94848) showing the location of the six deletion sites of MVA (-J-=junction of the deletion site). The "PPr+NPT II+IRES+EGFP+PPr+NS1" cassette was inserted into deletion 2 site of MVA. PPr=poxvirus promoter, NPT II=neomycin resistance gene (protein coding sequence), IRES=Internal Ribosome Binding Site and NS1=signal sequence plus NS1 protein coding sequence of dengue 2 NGC strain.

Figure 4:
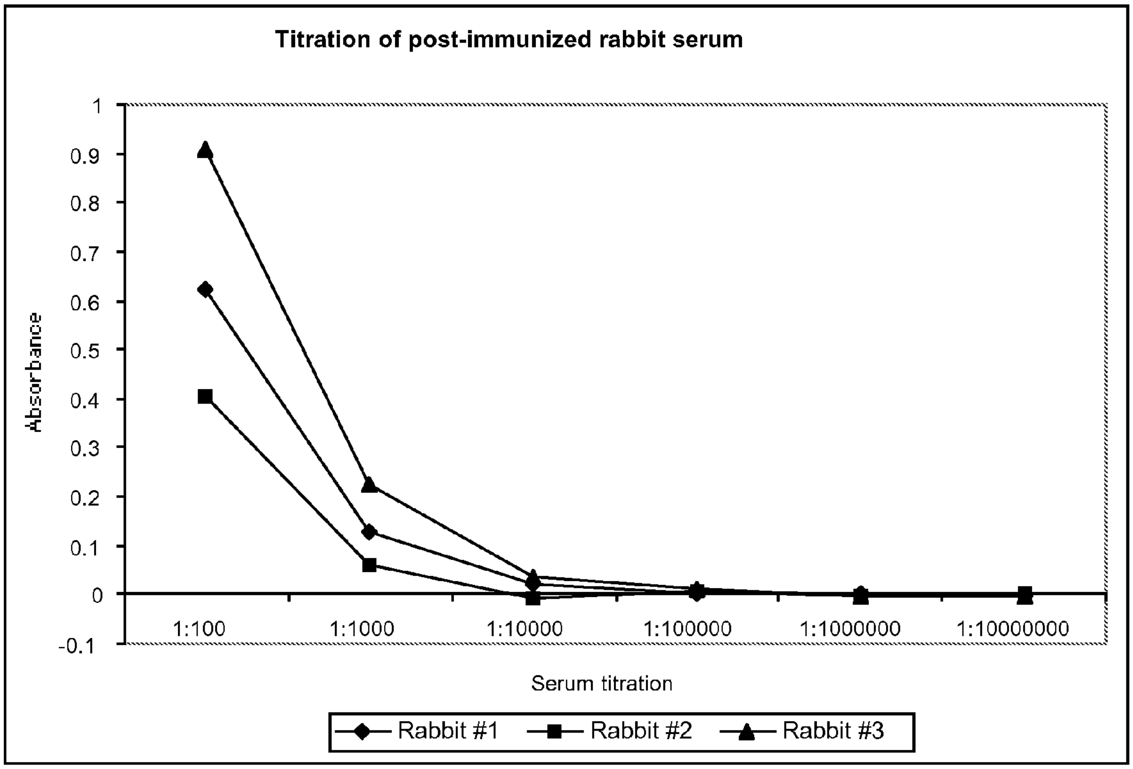

FIG. 4: Plot of the ELISA absorbance readings of the post-immunized sera titrations for all three rabbits.

Figure 5:
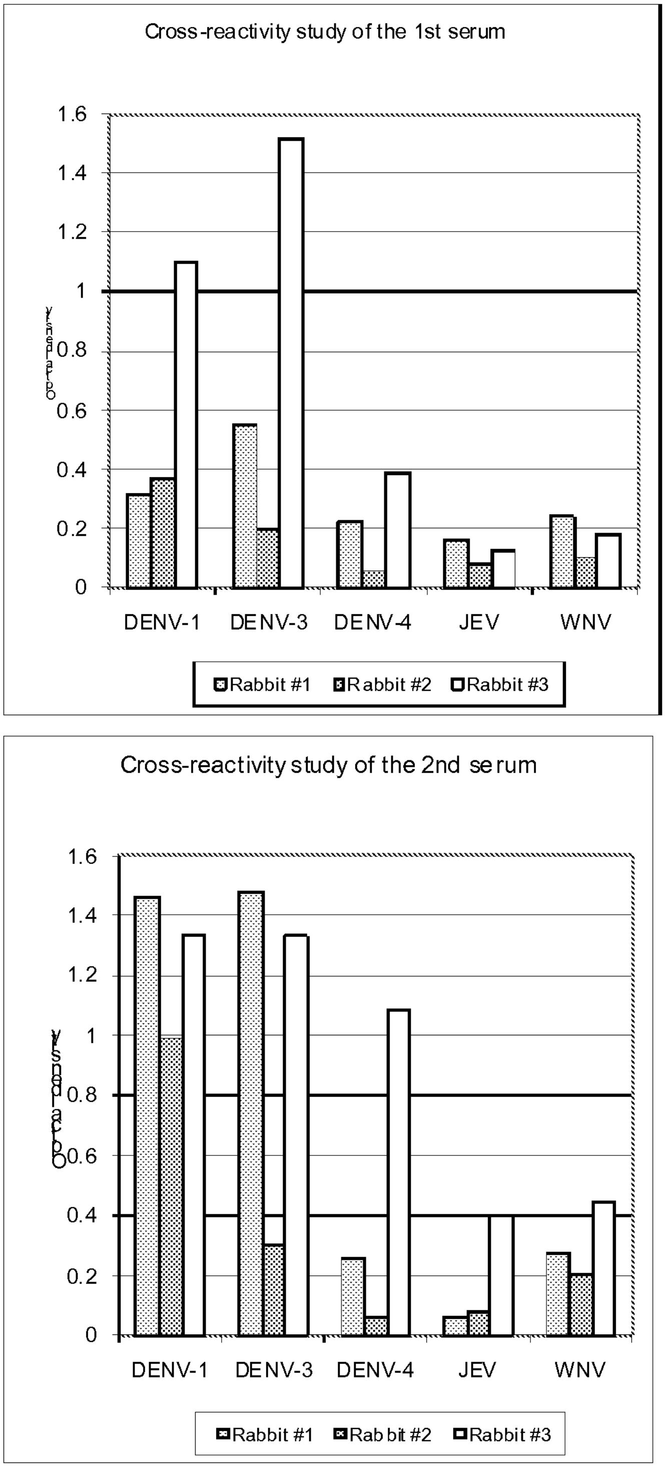

FIG. 5: Elisa cross reactivity studies. The cross reactivity of a rabbit serum of day 38 (upper part) and day 66 (lower part) with lysates of cells infected with DENV-1, DENV-3, DENV-4, JEV and WNV was tested in an ELISA-assay.

EXAMPLES

The following examples will further illustrate the present invention. It will be well understood by a person skilled in the art that the examples may not be interpreted in a way that limits the applicability of the technology provided by the present invention to these examples.

Example 1

Construction of mBN07

1. Details of NS1 Antigen (FIG. 1)

The example refers to NS1 of serotype 2 derived from the New Guinea. C strain—NGC strain (example: Genbank sequence AF038403). Since the NS1 protein of the Flaviviruses is produced as part of a polyprotein precursor the NS1 gene in the corresponding DNA is not preceded by a "ATG" start codon.

Therefore, a cDNA sequence coding for the NS1 protein must require the addition of a "ATG" start codon. This is then followed by the addition of a signal sequence so that the newly synthesized NS1 protein becomes glycosylated in the endoplasmic reticulum. Finally, the protein-coding cassette needs a stop codon and in this example TAG was added to the 3' terminal end of the protein coding cDNA sequence. In the example used in this invention the "ATG+signal sequence" element was derived from the hydrophobic C-terminal end of the E protein (the last 28 amino acids, which for NGC strains starts with the amino acid M (ATG)).

FIG. 1A shows the exact signal sequence plus NS1 sequence used as the example for this invention (see also SEQ:ID 5 and 6). The "signal sequence+NS1" nucleotide coding sequence was obtained by RT-PCR amplification from dengue NGC genomic RNA using the following primers:

D2NS 1-1 up:

(SEQ: ID No. 4)

5'-ACA*AGATCT*GGAATGAATTCACGTAGCACCTCA-3'

In italics: Bgl II restriction endonuclease recognition site. Underlined is the start codon.

D2NS1-2down:

(SEQ: ID No. 3)

5'-AAT*AGATCT*CTACTAGGCTGTGACCAAGGAGTT-3'

In italics: Bgl II restriction endonuclease recognition site. Underlined is the stop codon.

The RT-PCR amplification was carried out using the Titan One Tube RT-PCR kit from Roche Molecular Biochemical (Catalog number 1-939-823) following the instructions recommended by the manufacturer. However, essentially any commercial or non-commercial RT-PCR kit can be used instead.

The RT-PCR product can then be cloned into the BamHI site of any multiple cloning site present in many of the commercial bacterial cloning plasmids available but in this example it was cloned into pAF7 to give rise to clone to pAF7D2NS1—see FIGS. 1B and 1C for sequence details for pAF7D2NS1. FIG. 1D shows the hydrophobicity plots of NS1 amino acid sequence and NS1 containing the added signal sequence from the C-terminal amino acid coding sequence of E protein. The short N-terminal hydrophobic domain is indicative of a signal sequence.

2. Details of NS1 Expression Cassette (FIG. 2)

To express this "signal sequence+NS1" from a poxvirus vector such as canarypox, fowlpox, vaccinia or MVA, a poxvirus promoter needs to be added to the 5' end of this cDNA. Poly adenylation signal sequences are not required as all poxvirus synthesized RNAs are polyadenylated by a virally encoded enzyme that requires no polyA addition signal sequence for carrying out this function. Any poxvirus promoter can be used for the expression of this cassette. FIG. 2 and SEQ:ID No. 9 and 10 show the nucleotide sequence of the "poxvirus promoter+signal sequence+NS1" cassette used as the example in this invention.

For the example used in this invention the "signal sequence+NS1" was further PCR amplified from the NS1 plasmid clone using the primers oBN338 and oBN345. oBN345 primer contains a nucleotide sequence of a poxvirus minimal promoter element 5' to the target sequence within the cloning plasmid. Plasmid target sequence for oBN345 primer binding was approximately 40 nucleotides upstream of the signal sequence start codon. This was to ensure the RNA transcript contain a stretch of non-protein coding sequence before the signal sequence ATG start codon.

PCR primers with Ps promoter:

```
oBN338:
                                    (SEQ: ID No. 1)
5'-TTGTTAGCAGCCGGATCGTAGACTTAATTA (30 mer)

oBN345:
                                    (SEQ: ID No. 2)
5'-CAAAAAATTGAAATTTTATTTTTTTTTTTTGGAATATAAATAAAA

ACACGATAATACCATGG-3'

(Underlined nucleotides present the poxvirus
minimal promoter sequence.)
```

Annealing temperature for the PCR amplification reaction for the first five cycles was calculated from the nucleotide sequence that binds to the homologous sequence in the cloning vector of oBN345.

3. Integration of NS1 Expression Cassette into MVA (FIG. 3)

The PCR amplification product was blunt end cloned into the cut and blunt ended Xho I site of plasmid pBNX07 (see FIG. 3*a*) to form plasmid pBN41 (see FIG. 3*a*). pBN41 is the vector for integrating the "pox promoter+signal sequence+NS1" cassette into deletion site 2 of MVA by homologous recombination.

The essential features of pBN41 (see FIG. 3*a*) are as follows:

Plasmid backbone is pBluescript SK-plus from Stratagene (Genbank VB0078)

D2F1: Deletion 2 flank 1 homologous recombination arm. This represents the nucleotide sequence from 20117 to 20717 of the MVA Genbank sequence U94848.

PPr: Poxvirus promoter.

NPT II: Neomycin phoshotransferase protein coding sequence (protein coding sequence of Genbank V00618).

IRES: Internal Ribosome Entry Sequence from encephalomyocarditis virus (Jang et al., 1989, Genbank M16802).

EGFP: Enhanced Green Fluorescence Protein coding sequence (protein coding sequence—nucleotide 675 to nucleotide 1394 of Genbank sequence U57609)

NS1: "signal sequence+NS1" protein coding sequence from dengue NGC strain.

D2F2: Deletion 2 Flank 2 homologous recombination arm. This represents the nucleotide sequence from 20719 to 21343 of the MVA Genbank sequence U94848.

AmpR: Ampicillin resistance gene of pBluescript 3.1 Insertion of Dengue "Pox Promoter+Signal Sequence+NS1" into Deletion Site of MVA by Homologous Recombination 3.1.1 Integration into MVA Genome by Homologous Recombination The above integration vector pBN41 is used to integrate the dengue NS1 expression cassette plus also the reporter cassette (Pox promoter+NPT II-IRES-EGFP) into the MVA genome by homologous recombination between flank 1 and flank 2 arms of pBN41 and the homologous target sequences within the MVA genome. This is achieved by transfecting the linearized integration vector into chicken embryo fibroblast (CEF) cells previously infected with MVA at low multiplicity of infection (MOI, for example, 0.01 infectious units per cell). At 48 hours post infection or when the infection had reached confluency a viral extract is prepared and stored at −20° C. ready for selection and clone purification of desired recombinant MVA (rMVA).

3.1.2 Selection of rMVA and Clone Purification

The elimination of non-recombinant MVA (empty vector virus) and the amplification of rMVA is achieved by infection of confluent chicken embryo fibroblast (CEF) cells at low MOI in the presence of G418 (amount of G418 has to be optimize to determine the highest dose that dose not kill the CEF cells). Any virus that does not contain and integrated NPT II gene will not replicate in the presence of G418 added to the cell maintenance medium. G418 inhibits DNA replication but since the CEF cells will be in the stationary non-replicating state they will not be affected by the action of G418. CEF cells infected with rMVAs can be visualized under a fluorescence microscope due to the expression of the enhanced fluorescent green protein.

Viral extracts from the homologous recombination step must be serially diluted and used to infect fresh CEF cells in the presence of G418 and overlaid with low-melting point agarose. After 2 days of infection, the agarose-infected plates are observed under a fluorescent microscope for single foci of green infected cells. These cells are marked and agarose plugs containing the infected foci of cells are taken and placed into 1.5 ml microcentrifugation tubes containing sterile cell maintenance medium. Virus is released from the agarose plug by freeze-thawing the tube three times at −20° C.

The best clone or clones are further clone purified under agarose until by PCR analysis there is no signs of empty vector contamination (3 to 30 rounds of clone purification). These clones are then amplified for further stringent testing for correct insertion configuration, sequence verification of promoter-foreign gene cassette and expression analysis by RT-PCR. After these analysis only one clone was further amplified under G418 selection to prepare a master stock for further characterization and immunogenicity studies.

The recombinant MVA with the inserted dengue NS1 expression cassette described in this invention was named mBN07. FIG. 3*b* shows the configuration of inserted foreign sequence in mBN07.

4. Expression of Authentic NS1 by MVA

The expression of the NS1 protein from the recombinant MVA, mBN07, was verified by standard western blot analysis under non-denaturing conditions. More particularly, NS1 expression was analyzed after purified mBN07 was used to infect mammalian tissue culture cells, for example BHK-21 cells, at an MOI of 1.0 infectious unit per cell. Crude protein extracts were prepared from these infected cells 24-30 hours after infection where portions of these extract were mixed with SDS-PAGE gel loading buffer containing 2-mercaptoethanol (2-ME) or not containing 2-ME. These samples plus protein extract from cells (mosquito cell line) infected with dengue NGC strain as a positive control were electrophoretically separated in a SDS-PAGE gel and then blotted onto nitrocellulose membrane. The membrane was probed with an anti-dengue NS1 monoclonal antibody.

It was shown that NS1 expressed by mBN07 is recognized by the anti-dengue NS1 monoclonal antibody and forms the correct dimeric form similar to NS1 from dengue infected cells (compare unboiled mBN07 without 2-ME lane with unboiled DEN2 without 2-ME lane). Moreover it was shown that the dimeric form resolves out to the monomeric forms under denaturing conditions (see boiled mBN07 with 2-ME lane).

The NS1 expressed in cells infected with mBN07 was also recognized by pooled convalescent patients' sera and with monoclonal antibodies that cross-react to NS1 of all four serotypes of dengue in western blot analysis. This demonstrates that NS1 expressed by mBN07 is immunogenic.

Throughout the example section mBN07 (sometimes also termed BN07) is either stored in a liquid state (optionally frozen) or in a freeze-dried state. To obtain a freeze-dried virus a virus containing solution is prepared that comprises 10 mM Tris-buffer, 140 mM NaCl, 18.9 g/l Dextran (MW 36000-40000), 45 g/l sucrose, 0.108 g/l L-glutamic acid mono potassium salt monohydrate pH 7.4. Said formulation is then freeze-dried. For reconstitution water is added to the freeze-dried preparation.

Example 2

Cross Immunogencity of NS1 Expressed by mBN07 to NS1 of Dengue Viruses Other than Serotype 2 and to the NS1 of Japanese Encephalitis Virus (JEV) and West Nile Virus (WNV)

1. NS1 Expressed from mBN07: Reactivity to Patient Convalescent Sera

Tested was the possibility that NS1 expressed by mBN07 is recognized by convalescent patient sera from individuals who have evidence of previous dengue virus infection. Serum from 68 individuals who have antibodies against dengue virus envelope protein (by immunoblotting against authentic antigens prepared from Dengue serotypes 1 to 4) were selected for testing against immunoblot strips prepared from mBN07 infected cell extracts and MVA-GFP infected cell extracts as control. The antigen-containing cell lysates were treated with sample buffer without 2 mercaptoethanol and were not heated. Of the 68 individual sera tested, 62 (91.2%) reacted with BN07 NS1 expressed by mBN07 in immunoblots. These sera were further analyzed for reactivity to NS1 of all 4 dengue virus serotypes as well as Japanese encephalitis virus (JEV). The results are shown in Table 1. Fifty-four of the sera reacted with NS1 of all dengue virus serotypes and Japanese Encephalitis Virus (JEV), and 53 of these 54 sera (98.2%) also reacted with NS1 expressed from mBN07. Seven (7) sera were specific for NS1 of at least one dengue virus serotype and did not react with NS1 of JEV. All these 7 sera also reacted with NS1 expressed by mBN07. Another 7 sera reacted only with NS1 of JEV and not NS1 of any dengue virus serotype, yet 2 (28.6%) of these JEV-specific sera also reacted with NS1 expressed by mBN07.

TABLE 1

| | BN07 NS1 NEGATIVE | BN07 NS1 POSITIVE |
|---|---|---|
| AUTHENTIC DEN NS1 POSITIVE | 0% (0/7) | 100% (7/7) |
| AUTHENTIC DEN & JEV NS1 POSITIVE | 1.85% (1/54) | 98.15% (53/54) |
| AUTHENTIC JEV NS1 POSITIVE | 71.43% (5/7) | 28.57% (2/7) |

Comparison of antiserum reactions against authentic NS1 and NS1 expressed by mBN07. In brackets: Number of samples tested positive/Total number of samples tested. DEN = dengue, JEV = Japanese encephalitis virus.

The same 68 sera were also analyzed by reactivity against premembrane proteins. In the experience of the inventors, antibodies against premembrane are far more specific than antibodies against NS1 or E. Thus patients who have been infected with dengue will produce antibodies which recognize dengue virus premembrane and not JEV premembrane and vice versa. An analysis along these lines will provide a better prediction of the history of infection of individuals. Table 2 shows that sera from 22 patients reacted with authentic dengue premembrane protein alone thus suggesting that these 22 patients have been exposed to dengue virus only and not to JEV. All these 22 sera reacted with NS1 expressed by mBN07. Another 22 patients had evidence of previous infection with both dengue and JEV, and again all 22 sera also reacted with NS1 expressed by mBN07. In this series there were also 21 patients who had evidence of previous infection with JEV only (even though these sera had cross-reactive antibodies against dengue E). Interestingly, 17 of the 21 (82%) JEV responders reacted with NS1 expressed by mBN07. There were only 3 sera in the whole set that did not react with premembrane protein of either dengue or JEV and only 1 of these reacted with NS1 expressed by mBN07. The most likely reason for this is that the antibody titer is too low to be detected by immunoblotting.

TABLE 2

| | BN07 NS1 NEGATIVE | BN07 NS1 POSITIVE |
|---|---|---|
| AUTHENTIC DEN prM POSITIVE | 0% (0/22) | 100% (22/22) |
| AUTHENTIC DEN & JEV prM POSITIVE | 0% (0/22) | 100% (22/22) |
| AUTHENTIC JEV prM POSITIVE | 19.0% (4/21) | 81.0% (17/21) |
| PrM NEGATIVE | 66.7% (2/3) | 33.3% (1/3) |

Comparison of antiserum reactions against authentic premembrane and BN07 NS1. In brackets: Number of samples tested positive/Total number of samples tested. DEN = dengue, JEV = Japanese encephalitis virus.

The data in table 2 also clearly shows that of the 6 sera which did not react with NS1 expressed by mBN07, 4 were from individuals who had been previously infected with JEV and not dengue. The remaining 2 had no detectable antibodies to premembrane protein of either dengue or JEV and were likely to have been of a low titer.

2. mBN07 Vaccination of Rabbits and Testing of Post-Immunization Sera Against Dengue Virus and Japanese Encephalitis Virus Immunoblots and ELISA Assays Three specific pathogen-free rabbits were immunized by subcutaneous route according to the vaccination schedule as shown below. Each rabbit was vaccinated with one vial of freeze-dried vaccine (1×10e8 TCID50 BN07 freeze-dried vaccine) reconstituted to 1 ml with sterile water on day 0 and then again on day 28. Blood samples were taken prior to first vaccination (prebleed) and again 10 days after second vaccination.

| | |
|---|---|
| Day 0 = | prebleed followed by 1$^{st}$ vaccination |
| Day 28 = | 2$^{nd}$ vaccination |
| Day 38 = | blood sampling |
| Day 56 = | 3$^{rd}$ vaccination |
| Day 66 = | blood sampling |
| Day 112 = | 50 ml blood withdrawal from each rabbit |

2.1 Testing of Prebleed and Post-Immunization Sera Against Dengue Serotype 2 Immunoblots Dengue 2 virus antigens and antigens of uninfected C6/36 cells were separated by SDS PAGE under non-denaturing conditions. For immunoblot assays serum of day 38 (diluted 1:200) was used.

The results clearly demonstrated that upon vaccination with mBN07 all three rabbit produced anti-NS1 antibodies of high titres that cross react with authentic NS1 produced from a dengue serotype 2 infection of tissue culture mosquito cells. Serum taken before vaccination did not react to any of the dengue protein on the immunoblots.

Post-immunized serum of day 38 was titrated at 1:1000, 1:2000, 1:4000, $1:10^{-4}$, $1:10^{-5}$, $1:10^{-6}$ and tested on immunoblot strips of Dengue 2 virus antigens and control strips of uninfected C6/36 cells separated by SDS PAGE under non-denaturing conditions. Endpoint titers for the three rabbit sera of day 38 was calculated to be 1:10 000. The endpoint titers for the sera of day 66 were calculated to be $1\times10^5$ in both the immunoblot assay an the ELISA, respectively (data not shown).

Both, pre- and post-immunized serum were titrated at $1:10^{-2}$, $1:10^{-3}$, $1:10^{4}$, $1:10^{-5}$, $1:10^{-6}$, $1:10^{-7}$ and tested in indirect IgG ELISA. The wells were coated with dengue 2 and uninfected C6/36 lysates at 1:250 dilution.

TABLE 3

| | | $1:10^{-2}$ | $1:10^{-3}$ | $1:10^{-4}$ | $1:10^{-5}$ | $1:10^{-6}$ | $1:10^{-7}$ |
|---|---|---|---|---|---|---|---|
| Rabbit | Pre | −0.012 | 0.006 | 0.007 | 0.003 | −0.002 | 0.001 |
| #1 | Post | 0.623 | 0.127 | 0.02 | 0.004 | 0.001 | −0.003 |
| Rabbit | Pre | −0.012 | 0 | −0.001 | −0.003 | 0 | −0.001 |
| #2 | Post | 0.402 | 0.06 | −0.007 | 0.008 | −0.003 | 0.002 |
| Rabbit | Pre | −0.008 | 0.03 | −0.002 | 0.005 | −0.002 | −0.002 |
| #3 | Post | 0.907 | 0.224 | 0.038 | 0.011 | −0.001 | −0.003 |

ELISA absorbance reading for pre- and post-immunized serum from each rabbit at different dilutions (Pre = pre-immune sera, Post = post immunization sera).

The titration results for post-immunized sera of each rabbit were plotted as shown FIG. 4. The estimated endpoint titers for each rabbit post-immunized serum are 1:1000.

2.2 Testing of Prebleed and Post-Immunization Sera Against Dengue Serotype 1, 3, and 4, Japanese Encephalitis Virus and West Nile Virus Immunoblots Each of the rabbit serum of day 38 was tested at 1:1000 dilution on immunoblot strips of Dengue 1, 2, 3, 4 and JE virus antigens plus control strips of uninfected C6/36 cells separated by SDS PAGE under non-denaturing conditions. It was shown that each rabbit post-immunization sera reacts with NS1 from dengue serotypes 1, 3 and 4 as well as with NS1 on Japanese encephalitis immunoblots.

Each of the rabbit serum of day 66 was tested at 1:1000 dilution on immunoblot strips of Dengue 1, 3, 4, WNV and JE virus antigens plus control strips of uninfected C6/36 cells separated by SDS PAGE under non-denaturing conditions. It was shown that each rabbit post-immunization sera reacts with NS1 from dengue serotypes 1, 3 and 4 as well as with NS1 on Japanese encephalitis virus and West nile virus immunoblots.

To confirm the immunoblot assays Elisa cross reactivity assays were performed. The wells of microtiterplates were coated with DENV-1, DENV-3, DENV-4, JEV, WNV and uninfected cell lysates at 1:250 dilutions. The sera were sera from day 38 (FIG. 5A) and day 66 (FIG. 5B).

From the immunoblot assays as well as from the ELISA experiments it can be concluded that antibodies elicited by Dengue virus NS1 are cross reactive with all other Dengue serotypes, the JEV and the WNV.

2.3. Conclusions

Rabbits immunized with mBN07 vaccine elicited antibodies that recognize authentic Dengue virus serotype 2 NS1.

Very high immune response was observed where end points were $1:10^4$ and $1:10^{-3}$ in both immunoblot assays and ELISA respectively.

Antibodies elicited in the rabbits cross-reacted with all the other dengue serotypes (1, 3 & 4).

The antibodies also cross-reacted with NS1 from a heterologous virus such as JEV and WNV.

3. Immunogenicity Studies in Mice

Female out-bred mice were immunized by the intraperitoneal route with mBN07 expressing Dengue virus NS1 in different amounts and schedules as shown below. mBN08, a MVA corresponding to mBN07 but not expressing NS1 and PBS served as control. The serum of the mice was used to check whether the antibodies generated in the mice were able to react on Western blots with NS1 proteins from the different flavivirus serotypes and from the Japanese enzephalitis virus, respectively. The sera from the control mice were negative in all experiments.

The following groups were analyzed:

| Group | No. of mice | $1^{ST}$ dose | Interval | $2^{ND}$ dose | Interval before bleeding |
|---|---|---|---|---|---|
| 1 | 9 | $1\times10^7$ $TCID_{50}$ BN07 each (0.1 ml of vaccine diluted 1:5 in PBS/mouse) | 4 weeks | $1\times10^7$ $TCID_{50}$ BN07 each (0.1 ml of vaccine diluted 1:5 in PBS/mouse) | 3 weeks |
| 2 | 9 | $1\times10^7$ $TCID_{50}$ BN07 freeze-dried vaccine each (reconstituted in 1.2 ml water per mouse) | 4 weeks | $1\times10^7$ $TCID_{50}$ BN07 freeze-dried vaccine each (reconstituted in 1.2 ml water per mouse) | 3 weeks |
| 3 | 10 | $1\times10^7$ $TCID_{50}$ BN07 freeze-dried vaccine each (reconstituted in 1.2 ml water per mouse) | 3 weeks | $1\times10^7$ $TCID_{50}$ BN07 freeze-dried vaccine each (reconstituted in 1.2 ml water per mouse) | 4 weeks |
| 4 | 10 | $1\times10^7$ $TCID_{50}$ BN07 each (0.1 ml of vaccine diluted 1:5 in PBS/mouse) | 4 weeks | $1\times10^7$ $TCID_{50}$ BN07 each (0.1 ml of vaccine diluted 1:5 in PBS/mouse) | 4 weeks |
| 5 | 10 | $1\times10^7$ $TCID_{50}$ BN07 freeze-dried vaccine each (reconstituted in 1.2 ml water per mouse) | 4 weeks | $1\times10^7$ $TCID_{50}$ BN07 freeze-dried vaccine each (reconstituted in 1.2 ml water per mouse) | 4 weeks |

In the immunoblot experiments the following results were obtained:

| GROUP | NO. OF MICE TESTED | DENV-1 POSITIVE (% POS) | DENV-2 POSITIVE (% POS) | DENV-3 POSITIVE (% POS) | DENV-4 POSITIVE (% POS) | JEV POSITIVE (% POS) |
|---|---|---|---|---|---|---|
| 1 | 9 | 5 (55.5%) | 9 (100%) | 3 (33.3%) | 7 (77.7%) | 5 (55.5%) |
| 2 | 9 | 8 (88.8%) | 9 (100%) | 8 (88.8%) | 9 (100%) | 5 (55.5%) |
| 3 | 10 | 9 (90%) | 10 (100%) | 9 (90%) | 10 (100%) | 8 (80%) |
| 4 | 10 | 8 (80%) | 10 (100%) | 9 (90%) | 9 (90%) | 4 (40%) |
| 5 | 10 | 10 (100%) | 10 (100%) | 9 (100%) | 10 (100%0 | 8 (80%) |

Very similar experiments have been obtained with Balb/c mice: Mice were vaccinated with two shots of $1\times10^8$ $TCID_{50}$ BN07 (freeze-dried and reconstituted with water) at days 0 and 21. The sera were obtained at day 42. 100% of the sera reacted with Dengue virus 2 NS1, 100% of the sera reacted with NS1 proteins from all four Dengue virus serotypes and 75 of the sera reacted with the NS1 protein of JEV. The results obtained with $1\times10^8 TCID_{50}$ non-freeze dried BN07 were as follows: 100% of the sera reacted with NS1 from all four Denguevirus serotypes. The sera recognized NS1 from JEV not as good as the sera obtained from mice vaccinated with freeze-dried BN07.

Conclusion:

- 100% of the mice immunized with BN07 had antibodies to DENV-2 NS1 with very strong response.
- The immune response of mice immunized with 1×10e7 TCID50 BN07 was as strong as the immune response of mice immunized with 1×10e8 TCID50 BN07 (data not shown)
- The best cross-reactivity percentage were observed at with mice immunized at 4 weeks interval and 4 weeks before bleeding.
- Mice immunized with the BN07 freeze-dried vaccine were observed to have much stronger response to NS1 compared to those immunized with the non-freeze dried vaccine.

REFERENCES

Nimmannitya S, Kalayanaroo S, Nisalak A, and Innes B. 1990. Second attack of dengue hemorrhagic fever. Southeast Asian Journal of Tropical Medicine and Public Health, 21:699

Burke D S and Monath T P., 2001, Flaviviruses. In Fields Virology, Fourth Edition, Edited by David M Knipe and Peter M Howley. Published by Lippincott Williams and Wilkins, Philadelphia. Pages 1043-1125.

Flamand M, Megret F, Mathieu M, LePault, Rey F A and Deubel V., 1999. Dengue Virus Type 1 Nonstructural Glycoprotein NS1 is Secreted from mammalian cells as a soluble hexamer in a glycsylation-dependent fashion. J. Virol., 73:6104-6110.

Jang S K, Davies M V, Kaufman R J and Wimmer E., 1989. Initiation of protein synthesis by internal entry of ribosomes into the 5' nontranslated region of encephalomycarditis virus RNA in vivo. J. Virol., 63:1651-60.

Lindenbach B D and Rice C M., 2001, Flaviviruses and their replication. In Fields Virology, Fourth Edition, Edited by David M Knipe and Peter M Howley. Published by Lippincott Williams and Wilkins, Philadelphia. Pages 991-1041.

Schlesinger J J, Brandriss M W and Walsh E E., 1987. Protection of mice against dengue 2 virus encephalitis by immunization with the dengue 2 virus non-structural protein NS1. J. Gen. Virol., 68:853-7

Schesinger J J, Foltzer M and Chapman S., 1993. The Fc portion of antibody to yellow fever virus NS1 is a determinant of protection against yellow fever encephalitis in mice. Virology. 192: 132-41

The techniques and procedures described in this description are familiar to a skilled practitioner(s) in the art of molecular biology and virology especially relating to Flavivirus virology and genetic manipulation of poxviruses. The techniques and procedures described can be found in detail in the following literature resources:

Molecular Cloning, A laboratory Manual. Second Edition. By J. Sambrook, E. F. Fritsch and T. Maniatis. Cold Spring Harbor Laboratory Press. 1989.

Virology Methods Manual. Edited by Brian W J Mahy and Hillar O Kangro. Academic Press. 1996.

Molecular Virology: A Practical Approach. Edited by A J Davison and R M Elliott. The Practical Approach Series. IRL Press at Oxford University Press. Oxford 1993. Chapter 9: Expression of genes by vaccinia virus vectors.

Current Protocols in Molecular Biology. Publisher: John Wiley and Son Inc. 1998. Chapter 16, section IV: Expression of proteins in mammalian cells using vaccinia viral vector.

Antibodies, A Laboratory Manual. By Ed Harlow and David Lane. Cold Spring Harbor Laboratory Press. 1988.

The invention claimed is:

1. A method of inducing a cross-reactive immune response in an animal comprising:

a) providing an MVA virus vector encoding a Flavivirus NS1 protein of Dengue virus serotype 2;

b) administering the MVA virus vector to the animal;

c) expressing a dimeric, immunogenic, Flavivirus NS1 protein of Dengue virus serotype 2 in the animal from the MVA virus vector; and d) inducing a cross-reactive immune response in the animal against West Nile virus; and e) detecting the cross-reactive immune response.

2. The method of claim 1, wherein the expression cassette comprises a poxvirus promoter.

3. The method of claim 1, wherein the expression cassette further comprises a nucleic acid encoding the hydrophobic C-terminal end of the E-protein of a Flavivirus.

4. The method of claim 1, wherein the expression cassette comprises:

a transcriptional regulatory element;

an ATG initiation codon;

a sequence encoding a glycosylation signal sequence;

a sequence encoding an entire NS1 protein, or a part thereof, of Dengue Virus Serotype 2; and a translation termination codon.

5. The method of claim 1, wherein the expression cassette encodes a protein comprising the amino acid sequence set forth in SEQ ID NO:10.

6. The method of claim 1, wherein the MVA virus vector is characterized by being capable of reproductive replication in chicken embryo fibroblasts (CEF) and in the baby hamster kidney cell line BHK, but not capable of reproductive replication in vitro in the human keratinocyte cell line HaCaT.

7. The method of claim 1, comprising administering the MVA virus vector in a first inoculation ("priming inoculation") and in a second inoculation ("boosting inoculation").

8. The method of claim 1, wherein the animal is a human.

9. The method of claim 2, wherein the animal is a human.

10. The method of claim 3, wherein the animal is a human.

11. The method of claim 4, wherein the animal is a human.

12. The method of claim 5, wherein the animal is a human.

13. The method of claim 6, wherein the animal is a human.

14. The method of claim 7, wherein the animal is a human.

15. The method of claim 1 comprising detecting a cross-reactive immune response in the animal against Dengue virus serotype 1, Dengue virus serotype 3, Dengue virus serotype 4, Japanese Encephalitis virus, and West Nile virus.

16. The method of claim 8 comprising detecting a cross-reactive immune response in the animal against Dengue virus serotype 1, Dengue virus serotype 3, Dengue virus serotype 4, Japanese Encephalitis virus, and West Nile virus.

17. The method of claim 6 comprising detecting a cross-reactive immune response in the animal against Dengue virus serotype 1, Dengue virus serotype 3, Dengue virus serotype 4, Japanese Encephalitis virus, and West Nile virus.

18. The method of claim 13 comprising detecting a cross-reactive immune response in the animal against Dengue virus serotype 1, Dengue virus serotype 3, Dengue virus serotype 4, Japanese Encephalitis virus, and West Nile virus.

* * * * *

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: primer
```

-continued

<400> SEQUENCE: 1
ttgttagcag ccggatcgta gacttaatta 30

<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence:primer

<400> SEQUENCE: 2
caaaaaattg aaattttatt tttttttttt ggaatataaa taaaaacacg ataataccat 60
gg 62

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 3
aatagatctc tactaggctg tgaccaagga gtt 33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 4
acaagatctg gaatgaattc acgtagcacc tca 33

<210> SEQ ID NO 5
<211> LENGTH: 1143
<212> TYPE: DNA
<213> ORGANISM: Dengue virus type 2
<220> FEATURE:
<221> NAME/KEY: CDS
<222> LOCATION: (1)..(1140)
<223> OTHER INFORMATION: Signal sequence of Eprotein + NS1 coding sequence

<400> SEQUENCE: 5

```
atg aat tca cgc agc acc tca ctg tct gtg tca cta gta ttg gtg gga       48
Met Asn Ser Arg Ser Thr Ser Leu Ser Val Ser Leu Val Leu Val Gly
  1               5                  10                  15

gtc gtg acg ctg tat ttg gga gtt atg gtg cag gcc gat agt ggt tgc       96
Val Val Thr Leu Tyr Leu Gly Val Met Val Gln Ala Asp Ser Gly Cys
             20                  25                  30

gtt gtg agc tgg aaa aac aaa gaa ctg aag tgt ggc agt ggg att ttc      144
Val Val Ser Trp Lys Asn Lys Glu Leu Lys Cys Gly Ser Gly Ile Phe
         35                  40                  45

atc aca gac aac gtg cac aca tgg aca gaa caa tac aag ttc caa cca      192
Ile Thr Asp Asn Val His Thr Trp Thr Glu Gln Tyr Lys Phe Gln Pro
     50                  55                  60

gaa tcc cct tca aag cta gct tca gct atc cag aaa gct cat gaa gag      240
Glu Ser Pro Ser Lys Leu Ala Ser Ala Ile Gln Lys Ala His Glu Glu
 65                  70                  75                  80

ggc att tgt gga atc cgc tca gta aca aga ctg gaa aat ctg atg tgg      288
Gly Ile Cys Gly Ile Arg Ser Val Thr Arg Leu Glu Asn Leu Met Trp
                 85                  90                  95
```

-continued

```
aaa caa ata aca cca gaa ttg aat cac att cta tca gaa aat gag gtg      336
Lys Gln Ile Thr Pro Glu Leu Asn His Ile Leu Ser Glu Asn Glu Val
            100                 105                 110

aag ttg act att atg aca gga gac atc aaa gga atc atg cag gca gga      384
Lys Leu Thr Ile Met Thr Gly Asp Ile Lys Gly Ile Met Gln Ala Gly
        115                 120                 125

aaa cga tct ctg cag ccc cag ccc act gag ctg aag tat tca tgg aaa      432
Lys Arg Ser Leu Gln Pro Gln Pro Thr Glu Leu Lys Tyr Ser Trp Lys
    130                 135                 140

aca tgg ggc aaa gcg aaa atg ctc tct aca gag tct cat aac cag acc      480
Thr Trp Gly Lys Ala Lys Met Leu Ser Thr Glu Ser His Asn Gln Thr
145                 150                 155                 160

ttt ctc att gat ggc ccc gaa aca gca gaa tgc ccc aac aca aac aga      528
Phe Leu Ile Asp Gly Pro Glu Thr Ala Glu Cys Pro Asn Thr Asn Arg
                165                 170                 175

gct tgg aat tcg ctg gaa gtt gaa gac tat ggc ttt gga gta ttc acc      576
Ala Trp Asn Ser Leu Glu Val Glu Asp Tyr Gly Phe Gly Val Phe Thr
            180                 185                 190

acc aat ata tgg cta aag ttg aga gaa aag cag gat gta ttc tgc gac      624
Thr Asn Ile Trp Leu Lys Leu Arg Glu Lys Gln Asp Val Phe Cys Asp
        195                 200                 205

tca aaa ctc atg tca gcg gcc ata aaa gac aac aga gcc gtc cat gcc      672
Ser Lys Leu Met Ser Ala Ala Ile Lys Asp Asn Arg Ala Val His Ala
    210                 215                 220

gat atg ggt tat tgg ata gaa agt gca ctc aat gac aca tgg aag ata      720
Asp Met Gly Tyr Trp Ile Glu Ser Ala Leu Asn Asp Thr Trp Lys Ile
225                 230                 235                 240

gag aaa gcc tct ttc atc gaa gtt aaa agc tgc cac tgg cca aag tca      768
Glu Lys Ala Ser Phe Ile Glu Val Lys Ser Cys His Trp Pro Lys Ser
                245                 250                 255

cac acc ctc tgg agt aat gga gtg tta gaa agt gag atg ata att cca      816
His Thr Leu Trp Ser Asn Gly Val Leu Glu Ser Glu Met Ile Ile Pro
            260                 265                 270

aag aat ttc gct gga cca gtg tca caa cac aac tac aga cca ggc tac      864
Lys Asn Phe Ala Gly Pro Val Ser Gln His Asn Tyr Arg Pro Gly Tyr
        275                 280                 285

cat aca caa aca gca gga cca tgg cat cta ggt aag ctt gag atg gac      912
His Thr Gln Thr Ala Gly Pro Trp His Leu Gly Lys Leu Glu Met Asp
    290                 295                 300

ttt gat ttc tgc gaa gga acc aca gtg gtg gtg act gag gac tgt gga      960
Phe Asp Phe Cys Glu Gly Thr Thr Val Val Val Thr Glu Asp Cys Gly
305                 310                 315                 320

aat aga gga ccc tct tta aga aca act act gcc tct gga aaa ctc ata     1008
Asn Arg Gly Pro Ser Leu Arg Thr Thr Thr Ala Ser Gly Lys Leu Ile
                325                 330                 335

aca gaa tgg tgc tgc cga tct tgc aca tta cca ccg cta aga tac aga     1056
Thr Glu Trp Cys Cys Arg Ser Cys Thr Leu Pro Pro Leu Arg Tyr Arg
            340                 345                 350

ggt gag gac gga tgc tgg tac ggg atg gaa atc aga cca ttg aaa gag     1104
Gly Glu Asp Gly Cys Trp Tyr Gly Met Glu Ile Arg Pro Leu Lys Glu
        355                 360                 365

aaa gaa gag aat ttg gtc aac tcc ttg gtc aca gcc tag                 1143
Lys Glu Glu Asn Leu Val Asn Ser Leu Val Thr Ala
    370                 375                 380


<210> SEQ ID NO 6
<211> LENGTH: 380
<212> TYPE: PRT
<213> ORGANISM: Dengue virus type 2
```

<400> SEQUENCE: 6

```
Met Asn Ser Arg Ser Thr Ser Leu Ser Val Ser Leu Val Leu Val Gly
  1               5                  10                  15

Val Val Thr Leu Tyr Leu Gly Val Met Val Gln Ala Asp Ser Gly Cys
             20                  25                  30

Val Val Ser Trp Lys Asn Lys Glu Leu Lys Cys Gly Ser Gly Ile Phe
         35                  40                  45

Ile Thr Asp Asn Val His Thr Trp Thr Glu Gln Tyr Lys Phe Gln Pro
     50                  55                  60

Glu Ser Pro Ser Lys Leu Ala Ser Ala Ile Gln Lys Ala His Glu Glu
 65                  70                  75                  80

Gly Ile Cys Gly Ile Arg Ser Val Thr Arg Leu Glu Asn Leu Met Trp
                 85                  90                  95

Lys Gln Ile Thr Pro Glu Leu Asn His Ile Leu Ser Glu Asn Glu Val
            100                 105                 110

Lys Leu Thr Ile Met Thr Gly Asp Ile Lys Gly Ile Met Gln Ala Gly
        115                 120                 125

Lys Arg Ser Leu Gln Pro Gln Pro Thr Glu Leu Lys Tyr Ser Trp Lys
    130                 135                 140

Thr Trp Gly Lys Ala Lys Met Leu Ser Thr Glu Ser His Asn Gln Thr
145                 150                 155                 160

Phe Leu Ile Asp Gly Pro Glu Thr Ala Glu Cys Pro Asn Thr Asn Arg
                165                 170                 175

Ala Trp Asn Ser Leu Glu Val Glu Asp Tyr Gly Phe Gly Val Phe Thr
            180                 185                 190

Thr Asn Ile Trp Leu Lys Leu Arg Glu Lys Gln Asp Val Phe Cys Asp
        195                 200                 205

Ser Lys Leu Met Ser Ala Ala Ile Lys Asp Asn Arg Ala Val His Ala
    210                 215                 220

Asp Met Gly Tyr Trp Ile Glu Ser Ala Leu Asn Asp Thr Trp Lys Ile
225                 230                 235                 240

Glu Lys Ala Ser Phe Ile Glu Val Lys Ser Cys His Trp Pro Lys Ser
                245                 250                 255

His Thr Leu Trp Ser Asn Gly Val Leu Glu Ser Glu Met Ile Ile Pro
            260                 265                 270

Lys Asn Phe Ala Gly Pro Val Ser Gln His Asn Tyr Arg Pro Gly Tyr
        275                 280                 285

His Thr Gln Thr Ala Gly Pro Trp His Leu Gly Lys Leu Glu Met Asp
    290                 295                 300

Phe Asp Phe Cys Glu Gly Thr Thr Val Val Val Thr Glu Asp Cys Gly
305                 310                 315                 320

Asn Arg Gly Pro Ser Leu Arg Thr Thr Thr Ala Ser Gly Lys Leu Ile
                325                 330                 335

Thr Glu Trp Cys Cys Arg Ser Cys Thr Leu Pro Pro Leu Arg Tyr Arg
            340                 345                 350

Gly Glu Asp Gly Cys Trp Tyr Gly Met Glu Ile Arg Pro Leu Lys Glu
        355                 360                 365

Lys Glu Glu Asn Leu Val Asn Ser Leu Val Thr Ala
    370                 375                 380
```

<210> SEQ ID NO 7
<211> LENGTH: 1296
<212> TYPE: DNA
<213> ORGANISM: Dengue virus type 2

```
<220> FEATURE:
<221> NAME/KEY: CDS
<222> LOCATION: (50)..(1189)
<220> FEATURE:
<221> NAME/KEY: primer_bind
<222> LOCATION: (12)..(32)
<220> FEATURE:
<221> NAME/KEY: primer_bind
<222> LOCATION: (1243)..(1273)
<220> FEATURE:
<221> NAME/KEY: Misc_feature
<222> LOCATION: (1238)
<223> OTHER INFORMATION: n= a or c or g or t

<400> SEQUENCE: 7

ttttcctttg aaaaacacga taataccatg ggaattcccc cgatctgga atg aat tca      58
                                                      Met Asn Ser
                                                        1

cgc agc acc tca ctg tct gtg tca cta gta ttg gtg gga gtc gtg acg      106
Arg Ser Thr Ser Leu Ser Val Ser Leu Val Leu Val Gly Val Val Thr
     5                  10                  15

ctg tat ttg gga gtt atg gtg cag gcc gat agt ggt tgc gtt gtg agc      154
Leu Tyr Leu Gly Val Met Val Gln Ala Asp Ser Gly Cys Val Val Ser
 20                  25                  30                  35

tgg aaa aac aaa gaa ctg aag tgt ggc agt ggg att ttc atc aca gac      202
Trp Lys Asn Lys Glu Leu Lys Cys Gly Ser Gly Ile Phe Ile Thr Asp
                 40                  45                  50

aac gtg cac aca tgg aca gaa caa tac aag ttc caa cca gaa tcc cct      250
Asn Val His Thr Trp Thr Glu Gln Tyr Lys Phe Gln Pro Glu Ser Pro
             55                  60                  65

tca aag cta gct tca gct atc cag aaa gct cat gaa gag ggc att tgt      298
Ser Lys Leu Ala Ser Ala Ile Gln Lys Ala His Glu Glu Gly Ile Cys
         70                  75                  80

gga atc cgc tca gta aca aga ctg gaa aat ctg atg tgg aaa caa ata      346
Gly Ile Arg Ser Val Thr Arg Leu Glu Asn Leu Met Trp Lys Gln Ile
     85                  90                  95

aca cca gaa ttg aat cac att cta tca gaa aat gag gtg aag ttg act      394
Thr Pro Glu Leu Asn His Ile Leu Ser Glu Asn Glu Val Lys Leu Thr
100                 105                 110                 115

att atg aca gga gac atc aaa gga atc atg cag gca gga aaa cga tct      442
Ile Met Thr Gly Asp Ile Lys Gly Ile Met Gln Ala Gly Lys Arg Ser
                120                 125                 130

ctg cag ccc cag ccc act gag ctg aag tat tca tgg aaa aca tgg ggc      490
Leu Gln Pro Gln Pro Thr Glu Leu Lys Tyr Ser Trp Lys Thr Trp Gly
            135                 140                 145

aaa gcg aaa atg ctc tct aca gag tct cat aac cag acc ttt ctc att      538
Lys Ala Lys Met Leu Ser Thr Glu Ser His Asn Gln Thr Phe Leu Ile
        150                 155                 160

gat ggc ccc gaa aca gca gaa tgc ccc aac aca aac aga gct tgg aat      586
Asp Gly Pro Glu Thr Ala Glu Cys Pro Asn Thr Asn Arg Ala Trp Asn
    165                 170                 175

tcg ctg gaa gtt gaa gac tat ggc ttt gga gta ttc acc acc aat ata      634
Ser Leu Glu Val Glu Asp Tyr Gly Phe Gly Val Phe Thr Thr Asn Ile
180                 185                 190                 195

tgg cta aag ttg aga gaa aag cag gat gta ttc tgc gac tca aaa ctc      682
Trp Leu Lys Leu Arg Glu Lys Gln Asp Val Phe Cys Asp Ser Lys Leu
                200                 205                 210

atg tca gcg gcc ata aaa gac aac aga gcc gtc cat gcc gat atg ggt      730
Met Ser Ala Ala Ile Lys Asp Asn Arg Ala Val His Ala Asp Met Gly
            215                 220                 225

tat tgg ata gaa agt gca ctc aat gac aca tgg aag ata gag aaa gcc      778
Tyr Trp Ile Glu Ser Ala Leu Asn Asp Thr Trp Lys Ile Glu Lys Ala
        230                 235                 240
```

-continued

```
tct ttc atc gaa gtt aaa agc tgc cac tgg cca aag tca cac acc ctc      826
Ser Phe Ile Glu Val Lys Ser Cys His Trp Pro Lys Ser His Thr Leu
    245                 250                 255

tgg agt aat gga gtg tta gaa agt gag atg ata att cca aag aat ttc      874
Trp Ser Asn Gly Val Leu Glu Ser Glu Met Ile Ile Pro Lys Asn Phe
260                 265                 270                 275

gct gga cca gtg tca caa cac aac tac aga cca ggc tac cat aca caa      922
Ala Gly Pro Val Ser Gln His Asn Tyr Arg Pro Gly Tyr His Thr Gln
                280                 285                 290

aca gca gga cca tgg cat cta ggt aag ctt gag atg gac ttt gat ttc      970
Thr Ala Gly Pro Trp His Leu Gly Lys Leu Glu Met Asp Phe Asp Phe
            295                 300                 305

tgc gaa gga acc aca gtg gtg gtg act gag gac tgt gga aat aga gga     1018
Cys Glu Gly Thr Thr Val Val Val Thr Glu Asp Cys Gly Asn Arg Gly
        310                 315                 320

ccc tct tta aga aca act act gcc tct gga aaa ctc ata aca gaa tgg     1066
Pro Ser Leu Arg Thr Thr Thr Ala Ser Gly Lys Leu Ile Thr Glu Trp
    325                 330                 335

tgc tgc cga tct tgc aca tta cca ccg cta aga tac aga ggt gag gac     1114
Cys Cys Arg Ser Cys Thr Leu Pro Pro Leu Arg Tyr Arg Gly Glu Asp
340                 345                 350                 355

gga tgc tgg tac ggg atg gaa atc aga cca ttg aaa gag aaa gaa gag     1162
Gly Cys Trp Tyr Gly Met Glu Ile Arg Pro Leu Lys Glu Lys Glu Glu
                360                 365                 370

aat ttg gtc aac tcc ttg gtc aca gcc tagtagggat cgggggagct           1209
Asn Leu Val Asn Ser Leu Val Thr Ala
            375                 380

cactagtgga tccctccagc tcgagaggnc taattaatta agtctacgat ccggctgcta   1269

acaaagcccg aaaggaagct gagttgg                                        1296


<210> SEQ ID NO 8
<211> LENGTH: 380
<212> TYPE: PRT
<213> ORGANISM: Dengue virus type 2

<400> SEQUENCE: 8

Met Asn Ser Arg Ser Thr Ser Leu Ser Val Ser Leu Val Leu Val Gly
  1               5                  10                  15

Val Val Thr Leu Tyr Leu Gly Val Met Val Gln Ala Asp Ser Gly Cys
            20                  25                  30

Val Val Ser Trp Lys Asn Lys Glu Leu Lys Cys Gly Ser Gly Ile Phe
        35                  40                  45

Ile Thr Asp Asn Val His Thr Trp Thr Glu Gln Tyr Lys Phe Gln Pro
     50                  55                  60

Glu Ser Pro Ser Lys Leu Ala Ser Ala Ile Gln Lys Ala His Glu Glu
 65                  70                  75                  80

Gly Ile Cys Gly Ile Arg Ser Val Thr Arg Leu Glu Asn Leu Met Trp
                 85                  90                  95

Lys Gln Ile Thr Pro Glu Leu Asn His Ile Leu Ser Glu Asn Glu Val
            100                 105                 110

Lys Leu Thr Ile Met Thr Gly Asp Ile Lys Gly Ile Met Gln Ala Gly
        115                 120                 125

Lys Arg Ser Leu Gln Pro Gln Pro Thr Glu Leu Lys Tyr Ser Trp Lys
    130                 135                 140

Thr Trp Gly Lys Ala Lys Met Leu Ser Thr Glu Ser His Asn Gln Thr
145                 150                 155                 160
```

-continued

Phe Leu Ile Asp Gly Pro Glu Thr Ala Glu Cys Pro Asn Thr Asn Arg
165 170 175

Ala Trp Asn Ser Leu Glu Val Glu Asp Tyr Gly Phe Gly Val Phe Thr
180 185 190

Thr Asn Ile Trp Leu Lys Leu Arg Glu Lys Gln Asp Val Phe Cys Asp
195 200 205

Ser Lys Leu Met Ser Ala Ala Ile Lys Asp Asn Arg Ala Val His Ala
210 215 220

Asp Met Gly Tyr Trp Ile Glu Ser Ala Leu Asn Asp Thr Trp Lys Ile
225 230 235 240

Glu Lys Ala Ser Phe Ile Glu Val Lys Ser Cys His Trp Pro Lys Ser
245 250 255

His Thr Leu Trp Ser Asn Gly Val Leu Glu Ser Glu Met Ile Ile Pro
260 265 270

Lys Asn Phe Ala Gly Pro Val Ser Gln His Asn Tyr Arg Pro Gly Tyr
275 280 285

His Thr Gln Thr Ala Gly Pro Trp His Leu Gly Lys Leu Glu Met Asp
290 295 300

Phe Asp Phe Cys Glu Gly Thr Thr Val Val Val Thr Glu Asp Cys Gly
305 310 315 320

Asn Arg Gly Pro Ser Leu Arg Thr Thr Thr Ala Ser Gly Lys Leu Ile
325 330 335

Thr Glu Trp Cys Cys Arg Ser Cys Thr Leu Pro Pro Leu Arg Tyr Arg
340 345 350

Gly Glu Asp Gly Cys Trp Tyr Gly Met Glu Ile Arg Pro Leu Lys Glu
355 360 365

Lys Glu Glu Asn Leu Val Asn Ser Leu Val Thr Ala
370 375 380

<210> SEQ ID NO 9
<211> LENGTH: 1227
<212> TYPE: DNA
<213> ORGANISM: Dengue virus type 2
<220> FEATURE:
<221> NAME/KEY: promoter
<222> LOCATION: (5)..(48)
<223> OTHER INFORMATION: minimal poxvirus promoter element
<220> FEATURE:
<221> NAME/KEY: CDS
<222> LOCATION: (85)..(1224)
<223> OTHER INFORMATION: NS1

<400> SEQUENCE: 9
ctcgacaaaa aattgaaatt ttattttttt tttttggaat ataaataaaa acacgataat 60
accatgggaa ttccccgatc tgga atg aat tca cgc agc acc tca ctg tct 111
Met Asn Ser Arg Ser Thr Ser Leu Ser
1 5 gtg tca cta gta ttg gtg gga gtc gtg acg ctg tat ttg gga gtt atg 159
Val Ser Leu Val Leu Val Gly Val Val Thr Leu Tyr Leu Gly Val Met
10 15 20 25 gtg cag gcc gat agt ggt tgc gtt gtg agc tgg aaa aac aaa gaa ctg 207
Val Gln Ala Asp Ser Gly Cys Val Val Ser Trp Lys Asn Lys Glu Leu
30 35 40 aag tgt ggc agt ggg att ttc atc aca gac aac gtg cac aca tgg aca 255
Lys Cys Gly Ser Gly Ile Phe Ile Thr Asp Asn Val His Thr Trp Thr
45 50 55 gaa caa tac aag ttc caa cca gaa tcc cct tca aag cta gct tca gct 303
Glu Gln Tyr Lys Phe Gln Pro Glu Ser Pro Ser Lys Leu Ala Ser Ala
60 65 70

-continued

```
atc cag aaa gct cat gaa gag ggc att tgt gga atc cgc tca gta aca      351
Ile Gln Lys Ala His Glu Glu Gly Ile Cys Gly Ile Arg Ser Val Thr
     75                  80                  85

aga ctg gaa aat ctg atg tgg aaa caa ata aca cca gaa ttg aat cac      399
Arg Leu Glu Asn Leu Met Trp Lys Gln Ile Thr Pro Glu Leu Asn His
 90                  95                 100                 105

att cta tca gaa aat gag gtg aag ttg act att atg aca gga gac atc      447
Ile Leu Ser Glu Asn Glu Val Lys Leu Thr Ile Met Thr Gly Asp Ile
                110                 115                 120

aaa gga atc atg cag gca gga aaa cga tct ctg cag ccc cag ccc act      495
Lys Gly Ile Met Gln Ala Gly Lys Arg Ser Leu Gln Pro Gln Pro Thr
            125                 130                 135

gag ctg aag tat tca tgg aaa aca tgg ggc aaa gcg aaa atg ctc tct      543
Glu Leu Lys Tyr Ser Trp Lys Thr Trp Gly Lys Ala Lys Met Leu Ser
        140                 145                 150

aca gag tct cat aac cag acc ttt ctc att gat ggc ccc gaa aca gca      591
Thr Glu Ser His Asn Gln Thr Phe Leu Ile Asp Gly Pro Glu Thr Ala
    155                 160                 165

gaa tgc ccc aac aca aac aga gct tgg aat tcg ctg gaa gtt gaa gac      639
Glu Cys Pro Asn Thr Asn Arg Ala Trp Asn Ser Leu Glu Val Glu Asp
170                 175                 180                 185

tat ggc ttt gga gta ttc acc acc aat ata tgg cta aag ttg aga gaa      687
Tyr Gly Phe Gly Val Phe Thr Thr Asn Ile Trp Leu Lys Leu Arg Glu
                190                 195                 200

aag cag gat gta ttc tgc gac tca aaa ctc atg tca gcg gcc ata aaa      735
Lys Gln Asp Val Phe Cys Asp Ser Lys Leu Met Ser Ala Ala Ile Lys
            205                 210                 215

gac aac aga gcc gtc cat gcc gat atg ggt tat tgg ata gaa agt gca      783
Asp Asn Arg Ala Val His Ala Asp Met Gly Tyr Trp Ile Glu Ser Ala
        220                 225                 230

ctc aat gac aca tgg aag ata gag aaa gcc tct ttc atc gaa gtt aaa      831
Leu Asn Asp Thr Trp Lys Ile Glu Lys Ala Ser Phe Ile Glu Val Lys
    235                 240                 245

agc tgc cac tgg cca aag tca cac acc ctc tgg agt aat gga gtg tta      879
Ser Cys His Trp Pro Lys Ser His Thr Leu Trp Ser Asn Gly Val Leu
250                 255                 260                 265

gaa agt gag atg ata att cca aag aat ttc gct gga cca gtg tca caa      927
Glu Ser Glu Met Ile Ile Pro Lys Asn Phe Ala Gly Pro Val Ser Gln
                270                 275                 280

cac aac tac aga cca ggc tac cat aca caa aca gca gga cca tgg cat      975
His Asn Tyr Arg Pro Gly Tyr His Thr Gln Thr Ala Gly Pro Trp His
            285                 290                 295

cta ggt aag ctt gag atg gac ttt gat ttc tgc gaa gga acc aca gtg     1023
Leu Gly Lys Leu Glu Met Asp Phe Asp Phe Cys Glu Gly Thr Thr Val
        300                 305                 310

gtg gtg act gag gac tgt gga aat aga gga ccc tct tta aga aca act     1071
Val Val Thr Glu Asp Cys Gly Asn Arg Gly Pro Ser Leu Arg Thr Thr
    315                 320                 325

act gcc tct gga aaa ctc ata aca gaa tgg tgc tgc cga tct tgc aca     1119
Thr Ala Ser Gly Lys Leu Ile Thr Glu Trp Cys Cys Arg Ser Cys Thr
330                 335                 340                 345

tta cca ccg cta aga tac aga ggt gag gac gga tgc tgg tac ggg atg     1167
Leu Pro Pro Leu Arg Tyr Arg Gly Glu Asp Gly Cys Trp Tyr Gly Met
                350                 355                 360

gaa atc aga cca ttg aaa gag aaa gaa gag aat ttg gtc aac tcc ttg     1215
Glu Ile Arg Pro Leu Lys Glu Lys Glu Glu Asn Leu Val Asn Ser Leu
            365                 370                 375

gtc aca gcc tag                                                     1227
Val Thr Ala
        380
```

-continued

<210> SEQ ID NO 10
<211> LENGTH: 380
<212> TYPE: PRT
<213> ORGANISM: Dengue virus type 2

<400> SEQUENCE: 10

```
Met Asn Ser Arg Ser Thr Ser Leu Ser Val Ser Leu Val Leu Val Gly
  1               5                  10                  15

Val Val Thr Leu Tyr Leu Gly Val Met Val Gln Ala Asp Ser Gly Cys
             20                  25                  30

Val Val Ser Trp Lys Asn Lys Glu Leu Lys Cys Gly Ser Gly Ile Phe
         35                  40                  45

Ile Thr Asp Asn Val His Thr Trp Thr Glu Gln Tyr Lys Phe Gln Pro
     50                  55                  60

Glu Ser Pro Ser Lys Leu Ala Ser Ala Ile Gln Lys Ala His Glu Glu
 65                  70                  75                  80

Gly Ile Cys Gly Ile Arg Ser Val Thr Arg Leu Glu Asn Leu Met Trp
                 85                  90                  95

Lys Gln Ile Thr Pro Glu Leu Asn His Ile Leu Ser Glu Asn Glu Val
            100                 105                 110

Lys Leu Thr Ile Met Thr Gly Asp Ile Lys Gly Ile Met Gln Ala Gly
        115                 120                 125

Lys Arg Ser Leu Gln Pro Gln Pro Thr Glu Leu Lys Tyr Ser Trp Lys
    130                 135                 140

Thr Trp Gly Lys Ala Lys Met Leu Ser Thr Glu Ser His Asn Gln Thr
145                 150                 155                 160

Phe Leu Ile Asp Gly Pro Glu Thr Ala Glu Cys Pro Asn Thr Asn Arg
                165                 170                 175

Ala Trp Asn Ser Leu Glu Val Glu Asp Tyr Gly Phe Gly Val Phe Thr
            180                 185                 190

Thr Asn Ile Trp Leu Lys Leu Arg Glu Lys Gln Asp Val Phe Cys Asp
        195                 200                 205

Ser Lys Leu Met Ser Ala Ala Ile Lys Asp Asn Arg Ala Val His Ala
    210                 215                 220

Asp Met Gly Tyr Trp Ile Glu Ser Ala Leu Asn Asp Thr Trp Lys Ile
225                 230                 235                 240

Glu Lys Ala Ser Phe Ile Glu Val Lys Ser Cys His Trp Pro Lys Ser
                245                 250                 255

His Thr Leu Trp Ser Asn Gly Val Leu Glu Ser Glu Met Ile Ile Pro
            260                 265                 270

Lys Asn Phe Ala Gly Pro Val Ser Gln His Asn Tyr Arg Pro Gly Tyr
        275                 280                 285

His Thr Gln Thr Ala Gly Pro Trp His Leu Gly Lys Leu Glu Met Asp
    290                 295                 300

Phe Asp Phe Cys Glu Gly Thr Thr Val Val Val Thr Glu Asp Cys Gly
305                 310                 315                 320

Asn Arg Gly Pro Ser Leu Arg Thr Thr Thr Ala Ser Gly Lys Leu Ile
                325                 330                 335

Thr Glu Trp Cys Cys Arg Ser Cys Thr Leu Pro Pro Leu Arg Tyr Arg
            340                 345                 350

Gly Glu Asp Gly Cys Trp Tyr Gly Met Glu Ile Arg Pro Leu Lys Glu
        355                 360                 365

Lys Glu Glu Asn Leu Val Asn Ser Leu Val Thr Ala
    370                 375                 380
```